United States Patent
Sasaki et al.

(10) Patent No.: US 7,857,963 B2
(45) Date of Patent: *Dec. 28, 2010

(54) ELECTRODE PLATE FOR ELECTROCHEMICAL MEASUREMENTS

(75) Inventors: Hidehiro Sasaki, Osaka (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/683,502

(22) Filed: Jan. 7, 2010

(65) Prior Publication Data

US 2010/0101965 A1    Apr. 29, 2010

Related U.S. Application Data

(63) Continuation of application No. PCT/JP2009/001551, filed on Apr. 2, 2009.

(30) Foreign Application Priority Data

May 28, 2008    (JP)    ............... 2008-139764

(51) Int. Cl.
   *G01N 27/30*    (2006.01)
(52) U.S. Cl. ................ 205/775; 205/777.5; 204/400; 204/403.01; 204/411
(58) Field of Classification Search ............ 204/400, 204/403.1, 409, 411; 205/775, 777.5
   See application file for complete search history.

(56) References Cited

U.S. PATENT DOCUMENTS 5,437,999 A * 8/1995 Diebold et al. ......... 204/403.11

(Continued)

FOREIGN PATENT DOCUMENTS

EP    0 569 908 A2    11/1993

(Continued)

OTHER PUBLICATIONS

Horiuchi, T., et al., "Limiting Current Enhancement by Self-Induced Redox Cycling on a Micro-Macro Twin Electrode", J. Electrochem. Soc., Dec. 1991, pp. 3549-3553, vol. 138 No. 12, The Electrochemical Society, Inc.

(Continued)

*Primary Examiner*—Kaj K Olsen
(74) *Attorney, Agent, or Firm*—McDermott Will & Emery LLP

(57) ABSTRACT

To provide an electrode plate for electrochemical measurements that enables detecting and quantifying the concentration of a target substance contained in a sample solution with rapidity and favorable sensitivity using an apparatus for electrochemical measurements is objected to.

Specifically, the present invention is directed to a method of the determination using an electrode plate for electrochemical measurements 1 including a substrate 31, an upper layer 40 provided on the upper face of the substrate, a lower layer 11 provided on the lower face of the substrate, a first electrode body 32 sandwiched between the upper face of the substrate and the upper layer, and a second electrode body 12 sandwiched between the lower face of the substrate and the lower layer, wherein: the upper layer has a plurality of upper layer through-holes 41a and 41b; the first electrode body has a plurality of first electrodes 32d including a portion exposed from the upper face of the upper layer via the upper layer through-hole 41b; the substrate has a plurality of substrate through-holes 33; and the second electrode body has a plurality of second electrodes 12d including a portion exposed from the upper face of the upper layer via the upper layer through-hole 41a and the substrate through-hole in the second electrode body.

22 Claims, 24 Drawing Sheets

U.S. PATENT DOCUMENTS

| | | | |
|---|---|---|---|
| 7,635,422 B2 * | 12/2009 | Sasaki et al. | 205/775 |
| 2009/0145780 A1 | 6/2009 | Sasaki et al. | |
| 2009/0211922 A1 | 8/2009 | Sasaki et al. | |

FOREIGN PATENT DOCUMENTS

| | | |
|---|---|---|
| EP | 1 411 351 A1 | 4/2004 |
| JP | 02-268265 | 11/1990 |
| JP | 03-179248 | 8/1991 |
| JP | 03-238350 | 10/1991 |
| JP | 03-246460 | 11/1991 |
| JP | 04-136748 | 5/1992 |
| JP | 05-281181 | 10/1993 |
| JP | 06-027081 | 2/1994 |
| JP | 2006-078404 | 3/2006 |
| JP | 2006-250560 | 9/2006 |
| JP | 2006-322813 | 11/2006 |
| JP | 2007-010429 | 1/2007 |
| WO | WO 2009/057240 A1 | 5/2009 |

OTHER PUBLICATIONS

"Electrochemical Measurement Method in which Micro Electrode is used," pp. 48-49 and pp. 70-71, with an English translation thereof.

* cited by examiner (a)

(b)

US 7,857,963 B2

ELECTRODE PLATE FOR ELECTROCHEMICAL MEASUREMENTS

This is a continuation application under U.S.C 111(a) of pending prior International application No. PCT/JP2009/001551, filed on Apr. 2, 2009, which in turn claims the benefit of Japanese Application No. 2008-139764 filed on May 28, 2008, the disclosures of which Application are incorporated by reference herein.

1. TECHNICAL FIELD

The present invention relates to a method for detecting or quantifying a target substance contained in a sample solution, particularly a substance contained in a living body in a slight amount, an apparatus for electrochemical measurements, and an electrode plate for electrochemical measurements.

2. BACKGROUND ART

In recent years, electrode plates for electrochemical measurements for quantifying a saccharide such as sucrose, glucose contained in blood by a combination of a specific catalytic action of an enzyme and an electronic mediator having an electrode reaction activity have been developed. According to such an electrode plate for electrochemical measurements, after the reaction is allowed between the saccharide and the enzyme, the electronic mediator is electrochemically measured. Then the saccharide contained in the sample solution is quantified indirectly via the electronic mediator.

As one example, the electrode plate for electrochemical measurements is suitable for analyses of solution samples of a slight amount contained in living bodies. Thus, applications of the electrode plate for electrochemical measurements have been attempted to sensors through combining with a variety of organic materials or inorganic materials.

This method is highly specific for the saccharide, accompanied by less influences from the temperature during operation, and the mechanism of the quantifying device is simple; therefore, this method allows ordinary persons to quantify the blood glucose level easily at home.

The electrode response speed of the electrode plate for electrochemical measurements is accelerated as the area of a microelectrode carried by the electrode plate for electrochemical measurements is reduced. Therefore, various electrode shapes, and miniaturization of electrodes have been investigated. However, as the area of the electrode is reduced, the resulting electric current value is lowered. For example, when the area of the electrode is miniaturized to approximately several hundred $\mu m^2$, detectable electric current value may be lowered to several ten to several nA order. Thus, increase in noise response, and deterioration of the sensitivity may be caused at the time of measurement. Accordingly, in order to avoid these defects, electrode plates for electrochemical measurements in which a plurality of microelectrodes are integrated were studied as in Patent Documents 1 to 4.

Patent Documents 1 to 4 propose methods of producing a large quantity of microelectrodes on a substrate while keeping a constant distance between adjacent microelectrodes with favorable reproducibility.

FIG. 18 shows an overall view (FIG. 18($a$)) and a partial enlarged view (FIG. 18($b$)) of the construction of a conventional electrode plate for electrochemical measurements disclosed in Patent Document 1. The electrode plate for electrochemical measurements 200 is constructed by laminating an insulative substrate 201, a bottom electrode body 202 that functions as an oxidation electrode, an insulating layer 203, and a surface electrode 204 that functions as a reduction electrode. A large number of cylindrical micropores 205 are formed on the surface of the surface electrode 204, and the film face of the bottom electrode body 202 is exposed to the micropore 205.

The insulative substrate 201 is composed of, for example, a silicon substrate with an oxide film, generally referred to, in which oxide film 201$b$ is adhered on the main surface of silicon substrate 201$a$. The bottom electrode body 202 is an oxidation electrode formed with a metal, a semimetal, a carbonic material, or a semiconductor on the surface of the oxide film 201$b$ of the substrate 201 (i.e., insulator surface). The surface electrode 204 is a reduction electrode formed with a metal, a semimetal, or a semiconductor on the insulating layer 203, similarly to the bottom electrode body 202.

A working electrode pair, i.e., paired oxidation electrode and reduction electrode, is formed with an exposed part of the bottom electrode body 202 from micropore 205 (hereinafter, referred to as oxidation electrode 202$a$), and the surface electrode 204. In other words, both the oxidation electrode 202$a$ and the surface electrode 204 function as working electrodes, and more specifically, the exposed part of the bottom electrode body 202 functions as an oxidation electrode, while the surface electrode 204 functions as a reduction electrode, as described above. In FIG. 18, the reference numeric character 206 represents an opening for drawing the electrode, opened so as to connect an outer lead to one end of the bottom electrode body 202. Herein, the micropore 205 represents a hole that completely penetrates through the insulating layer 203 and the surface electrode 204, and then reaches to the surface of the bottom electrode body 202.

In an apparatus for electrochemical measurements in which the electrode plate for electrochemical measurements as described above is used, a potential is applied to the bottom electrode body 202 and the surface electrode 204 for achieving an electric current response. When the apparatus for electrochemical measurements is constructed with three electrodes, i.e., the oxidation electrode body 202$a$, surface electrode 204, and a counter electrode (not shown in the Figure), a potential is applied between the oxidation electrode body 202$a$ and the counter electrode, and between the surface electrode 204 and the counter electrode, provided that the potential shown by the counter electrode in the sample solution is zero.

In addition, when the apparatus for electrochemical measurements is constructed with four electrodes, i.e., the oxidation electrode body 202$a$, surface electrode 204, a reference electrode (not shown in the Figure), and an auxiliary electrode (not shown in the Figure), a potential is applied between the oxidation electrode body 202$a$ and the reference electrode, and between the surface electrode 204 and the reference electrode, provided that the potential shown by the reference electrode in the sample solution is zero.

Patent Document 4 and Nonpatent Document 1 propose an electrode plate for electrochemical measurements in which cylindrical micropores 205 are provided such that the intervals among them become greater than their diameter, and report the results of electrochemical measurements using the same. In these Documents, the surface electrode 204 that is a macroelectrode has an area greater than the bottom electrode that is an assembly of microelectrodes. At the time of measurement, potentials are applied, respectively, which can cause an oxidative reaction on the oxidation electrode body 202$a$, and a reductive reaction on the surface electrode 204. It is reported that self-induced redox cycle is thus generated between the oxidation electrode body 202a and the surface electrode 204, and then apparently high electric current response can be achieved.

In this manner, a target substance such as a saccharide is quantified via an electronic mediator that is present in a sample solution. Alternatively, even though a potential that causes a reductive reaction is applied on the oxidation electrode body 202a, while a potential that causes an oxidative reaction is applied on the surface electrode 204, similar self-induced redox cycle is generated.

Hereinbelow, the self-induced redox cycle described in Patent Document 4, and Nonpatent Documents 1 and 2 is explained with reference to FIG. 19.

The self-induced redox cycle in FIG. 19 proceeds on two working electrodes, i.e., microelectrode 221 and macroelectrode 222. An oxidative reaction of reductant 224 is caused to produce oxidant 225 on the surface of the microelectrode 221, and then the oxidation current flows to the microelectrode 221. On the surface of a part 222a, which is close to the microelectrode 221, of the macroelectrode 222, the oxidant 225 is reduced to be converted into reductant 226, and then the reductive electric current flows to the macroelectrode 222. Furthermore, the reductant 225 is diffused to reach to the surface of the microelectrode 221, and then an oxidative reaction is caused again from the reductant 224 to the oxidant 225, and oxidation current flows toward the microelectrode 221.

As a consequence, the reductant 224 can be fed to the surface of the microelectrode 221 by reducing the oxidant 225 generated from the microelectrode 221 to give the reductant 226 on the surface of the macroelectrode 222a. Accordingly, as a result of occurrence a so-called redox cycle reaction in which an oxidative reaction and a reductive reaction recur between the microelectrode 221 and the macroelectrode 222a, an electric current constantly flows to the microelectrode 221, and thus the target substance contained in a sample solution in a slight amount can be detected and quantified. Moreover, in order to improve the efficacy of the measurement with high sensitivity, electrode pairs consisting of an oxidation electrode and a reduction electrode by which a redox cycle proceeds are formed as many as possible through forming a larger number of the microelectrodes 221 on the substrate.

Patent Document 1: Japanese Patent Publication No. 2556993 (page 6, FIG. 1)

Patent Document 2: Japanese Patent Publication No. 2564030 (page 7, FIG. 2)

Patent Document 3: Japanese Patent Laid-Open Publication No. 2006-78404 (page 25, FIG. 1)

Patent Document 4: Japanese Patent Publication No. 3289059 (page 16, FIG. 5)

Patent Document 5: Japanese Patent Laid-Open Publication No. 2007-010429 (FIG. 3, FIG. 4)

Nonpatent Document 1: J. Electrochem. Soc., Vol. 138, No. 12, page 3551

Nonpatent Document 2: Koichi Aoki et al., "Electrochemical Measurement Method Using Microelectrode" edited by The Institute of Electronics, Information and Communication Engineers, published on Feb. 10, 1998 pages 48-49 and 70-71

DISCLOSURE OF THE INVENTION

As shown in FIG. 18, when the area of the surface electrode 204 that functions as a reduction electrode is much greater than the area of oxidation electrode 202a, problems as in the following are caused.

Although reductant 226 formed on macroelectrode 222a is diffused, it reaches not only to the microelectrode 221 (corresponding to oxidation electrode body 202a in FIG. 18), but in part, also onto apart 222b, which is far from the microelectrode 221, of the macroelectrode 222 (corresponding to surface electrode 204 in FIG. 18) as shown in FIG. 19, right side. Such a reductant 227 is converted into oxidant 228 by an oxidative reaction. In other words, an oxidative reaction is also caused on the macroelectrode 222 (see, also FIG. 4 in Japanese Patent Laid-Open Publication No. Hei 3-246460).

Next, the oxidant 228 is diffused, and reaches onto a part 222a, which is close to the microelectrode 221, of the macroelectrode 222. The oxidant 228 is converted into the reductant 226 there by a reductive reaction. The reductant 226 is diffused, reaches onto the surface of the microelectrode 221, and oxidized again to be converted into oxidant 225 (alternatively, reaches again to a part 222b, which is far from the microelectrode 221, of the macroelectrode 222).

Accordingly, on the surface electrode 204 shown in FIG. 18, an oxidative reaction occurs concurrently with a reductive reaction. As a result, an oxidation reaction of the reductant, the detection of which should be effected on the oxidation electrode body 202a, is also caused on the surface electrode 204 concurrently. Therefore, the reductant generated on the surface electrode 204 is not oxidized efficiently on the oxidation electrode body 202a to lead to problems in improvement of sensitivity. In addition, since the surface electrode 204 operates as a macroelectrode, a great charge current is achieved in applying the potential. Thus, a problem of lengthening of the time required until the reaction reaches to a stationary state as compared with the oxidation electrode body 202a that is a microelectrode has also caused.

The present invention was made in order to solve the problems described above, and an object of the invention is to provide a method of quantifying the concentration of a target substance such as a saccharide contained in a sample solution with rapidity and high sensitivity, and an apparatus for electrochemical measurements, as well as an electrode plate for electrochemical measurements which can be used in the method and the apparatus.

In order to solve the problems described above, an aspect of the present invention is directed to a method of detecting or quantifying a target substance contained in a sample solution by way of an apparatus for electrochemical measurements comprising a reference electrode, an auxiliary electrode and an electrode plate for electrochemical measurements, or a counter electrode and an electrode plate for electrochemical measurements. Details of aspects of the present invention are as in the following.

The sample solution contains an electronic mediator, and the electrode plate for electrochemical measurements consists of a first electrode plate or a second electrode plate. The first electrode plate and the second electrode plate comprise a substrate made of an insulator, an upper layer made of an insulator provided on the upper face of the substrate, a lower layer made of an insulator provided on the lower face of the substrate, a first electrode body sandwiched between the upper face of the substrate and the upper layer, and a second electrode body sandwiched between the lower face of the substrate and the lower layer.

The upper layer has a plurality of substrate through-holes extending through from the upper face to the lower face of the upper layer. The first electrode body has a plurality of first electrodes composed of a portion exposed from the upper face of the upper layer via the upper layer through-hole. The substrate has a plurality of substrate through-holes extending through from the upper face to the lower face of the substrate, and the second electrode body has a plurality of second electrodes composed of a portion exposed from the upper face of the upper via the upper layer through-holes and the substrate through-holes.

On a plane view of the first electrode plate: any of the plurality of substrate through-holes does not overlap with the first electrode; four or more second electrodes having substantially the same area are disposed around the each first electrode, with an even distance between centers of the first electrode and each of the second electrodes; two first electrodes having substantially the same area are disposed around the each second electrode, with an even distance between centers of the second electrode and each of the first electrodes; and the area of the each first electrode and total area of the second electrodes therearound are substantially the same.

on a plane view of second electrode plate, any of the plurality of substrate through-holes does not overlap with the first electrode; four or more first electrodes having substantially the same area are disposed around the each second electrode, with an even distance between centers of the second electrode and each of the first electrodes; two second electrodes having substantially the same area are disposed around the each first electrode, with an even distance between centers of the first electrode and each of the second electrodes; and the area of the each second electrode and total area of the first electrodes therearound are substantially the same.

The method comprises the following steps: the step of bringing the reference electrode, the auxiliary electrode and the electrode plate for electrochemical measurements, or the counter electrode and the electrode plate for electrochemical measurements into contact with the sample solution; the step of sweeping a positive potential to either one of the first electrode body and the second electrode body, and applying a negative potential to the other one, or applying a positive potential to either one of the first electrode body and the second electrode body, and sweeping a negative potential to the other one, to measure the electric current between the first electrode body and the second electrode body; and the step of calculating the amount of the target substance or detecting the target substance on the basis of the electric current.

In another aspect, the present invention is directed to the aforementioned apparatus for electrochemical measurements, the first electrode plate, or the second electrode plate.

The first electrode plate may be constructed such that a plurality of covering insulators that adjust the area of the portion exposed from the upper face of the upper layer are provided on the first electrode body. In this construction, the covering insulator may be provided on the each first electrode, and on a plane view, the each first electrode and the covering insulator provided on the each first electrode may share a common center point, while the outer edge of them may have a similar shape.

In the first electrode plate, the shape of the first electrode is preferably a square (regular tetragon) or a regular hexagon on a plane view.

The second electrode plate may be constructed such that a plurality of covering insulators that adjust the area of the portion exposed from the upper face of the upper layer are provided on the second electrode body. In this construction, the covering insulator may be provided on the each second electrode, and on a plane view, the each second electrode and the covering insulator provided on the each second electrode may share a common center point, while the outer edge of them may have a similar shape.

In the second electrode plate, the shape of the second electrode is preferably a square or a regular hexagon on a plane view.

In the first electrode plate or the second electrode plate, the first electrode body may be composed of a metal plate including all the plurality of the first electrodes. Also, the second electrode body may be composed of a metal plate including all the plurality of the first electrodes.

The area of the electrode referred to herein means the surface area of the electrode.

The aforementioned and other objects, features, and advantages of the present invention are clarified by the following detailed description of preferred embodiments with reference to accompanying drawings.

The method of detecting or quantifying a target substance contained in a sample solution according to the present invention enables a target substance to be detected with rapidity and high sensitivity. In addition, according to the electrode plate for electrochemical measurements of the present invention, even amount of the reaction products can be kept on a plurality of electrodes, and a reaction which may result in the noise can be suppressed. Therefore, use of the same enables the target substance contained in a sample solution to be detected or quantified with rapidity and favorable sensitivity, and also with high accuracy.

DETAILED DESCRIPTION OF THE INVENTION

Hereinafter, embodiments of the present invention are explained with reference to accompanying drawings.

Embodiment 1

Figure 1:
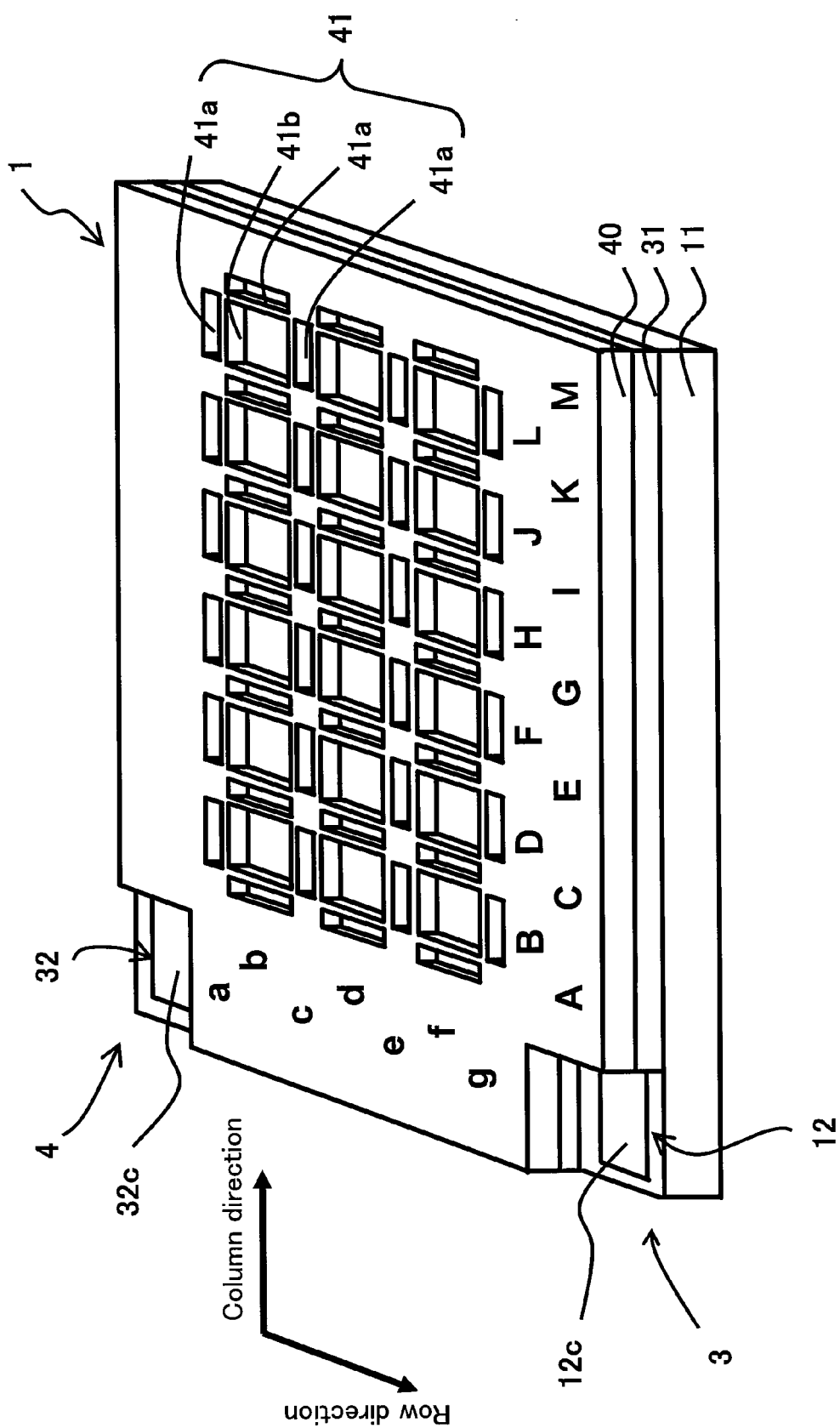
FIG. 1 shows a perspective view schematically illustrating an electrode plate for electrochemical measurements according to Embodiment 1.

FIG. 1 shows a perspective view schematically illustrating the electrode plate for electrochemical measurements according to Embodiment 1. In the construction of electrode plate for electrochemical measurements 1, lower layer 11, substrate 31, and upper layer 40 are laminated in this order from the under side, with second electrode body 12 being sandwiched between the lower layer 11 and the substrate 31, and with first electrode body 32 being sandwiched between the substrate 31 and the upper layer 40.

On the upper layer 40, a plurality of upper layer through-holes 41*a* and 41*b* are formed to give a matrix shape. When the terms must be strictly distinguished, the upper layer through-hole 41*a* is referred to as first upper layer through-hole. Similarly, the upper layer through-hole 41*b* is referred to as second upper layer through-hole 41*b*.

In FIG. 1, when the lateral direction is defined as row direction, and the lengthwise direction is defined as column direction, positions where the upper layer through-holes 41 are formed in the row direction are designated A, B, C, D, . . . and M in sequence, and positions in the column direction are designated as a, b, c, d . . . and g in sequence. Additionally, upper layer through-hole 41 (X, x) represents the upper layer through-hole 41 situated at X (X=A, B, C, D, . . . or M) in the row direction, and at x (x=a, b, c, d, . . . or g) in the column direction.

Among the upper layer through-holes 41, the larger upper layer through-holes 41*b* are formed in the number of 18 in total, with each six along the row direction and each three along the column direction. In addition, smaller upper layer through-holes 41*a* having a long side along the row direction are formed in the number of 24 in total, with each six along the row direction and each four along the column direction, while smaller upper layer through-holes 41*a* having a long side along the column direction are formed in the number of 21, with each seven along the row direction and each three along the column direction. On the plane view, the shape of each upper layer through-hole 41*b* is a square, and the shape of each upper layer through-hole 41*a* is a rectangle having a long side of substantially the same length as the length of the side of the upper layer through-hole 41*b*.

The upper layer through-holes 41*b* that allow the first electrode body 32 to be exposed to the upper face of the electrode plate for electrochemical measurements 1, and the upper layer through-holes 41*a* that allow the second electrode body 12 to be exposed to the upper face of the electrode plate for electrochemical measurements 1 are alternately disposed at regular intervals. The upper layer through-holes 41*a* allow the second electrode body 12 to be exposed to the upper face of the electrode plate for electrochemical measurements 1 via the substrate through-hole on the substrate 31 not shown in FIG. 1. The electrode plate for electrochemical measurements 1 has a notch 3 which is formed such that second electrode lead 12*c* provided with the second electrode body 12 is exposed in the vicinity of the end, and notch 4 which is formed such that first electrode lead 32*c* provided as a member of the first electrode body 32 is exposed in the vicinity of the end.

Figure 2:
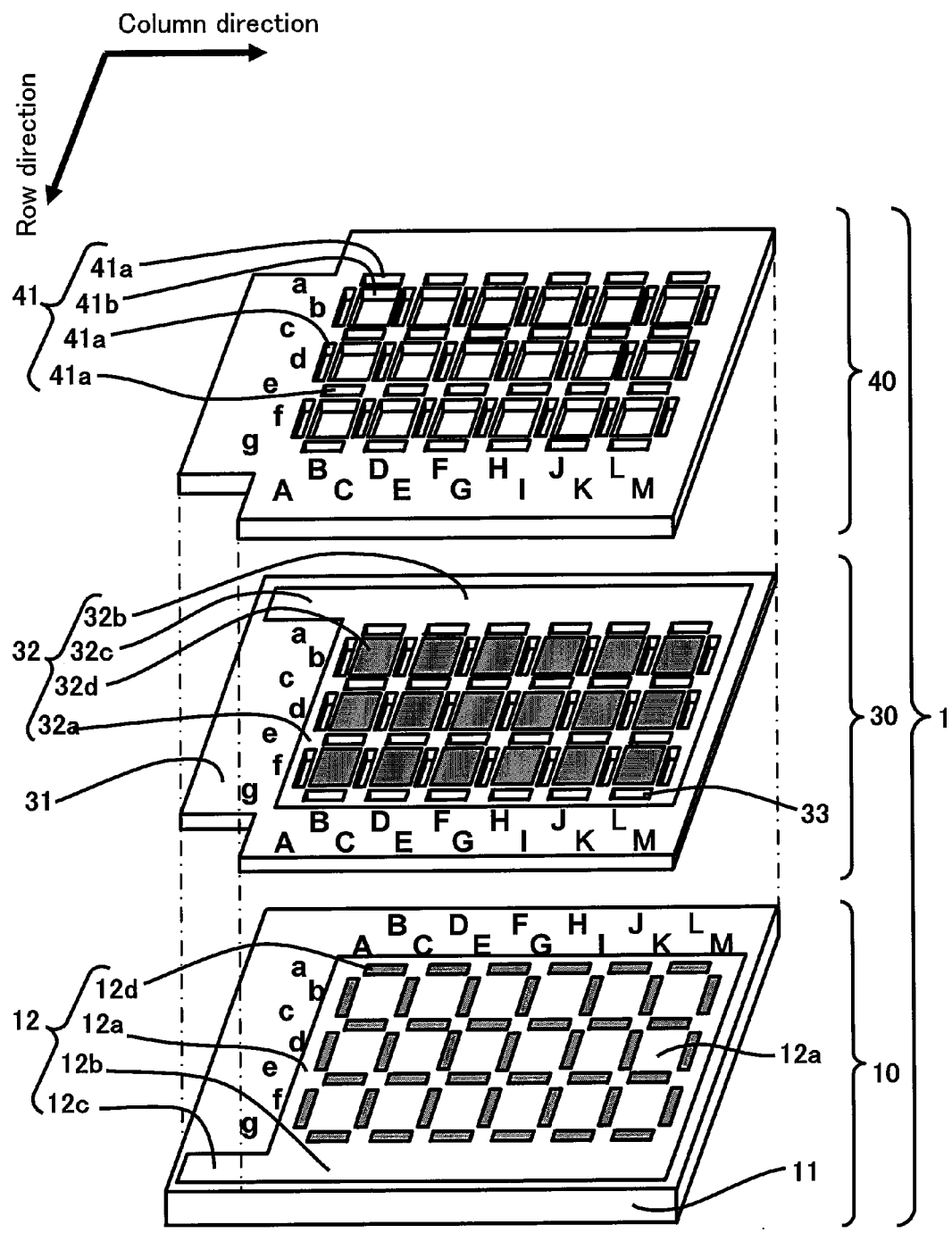
FIG. 2 shows an exploded perspective view schematically illustrating the electrode plate for electrochemical measurements according to Embodiment 1.

FIG. 2 shows an exploded perspective view illustrating the electrode plate for electrochemical measurements 1 shown in FIG. 1. As is shown in FIG. 2, in the electrode plate for electrochemical measurements 1 according to Embodiment 1, second electrode body-mounted layer 10, first electrode body-mounted layer 30, and upper layer 40 are laminated in this order from the under side.

The second electrode body-mounted layer 10 is composed of lower layer 11, and second electrode body 12 provided on the upper face of the lower layer 11. The first electrode body-mounted layer 30 is composed of substrate 31, and first electrode body 32 provided on the upper face of the substrate 31. The lower layer 11, substrate 31, upper layer 40 are all insulators. The second electrode body 12 is sandwiched between the lower layer 11 and the substrate 31 as shown in FIG. 2. Similarly, the first electrode body 32 is sandwiched between the substrate 31 and the upper layer 40. The upper layer 40 has a plurality of upper layer through-holes 41.

In FIG. 2, the upper layer through-holes 41 are provided according to a similar arrangement to that shown in FIG. 1. A part of the first electrode body 32 is exposed from the upper layer through-hole 41*b* (B, b) positioned at the upper left, and also from the upper layer through-holes 41*b* arranged in the row direction (D, b), (F, b), . . . and the column direction (B, d), (B, f) starting at the upper layer through-hole (B, b) 41*b* as a base point, among these upper layer through-holes 41. Of the first electrode body 32, the parts exposed from each upper layer through-hole 41*b*, i.e., gray-colored portions on the first electrode body 32 in FIG. 2 are brought into contact with the sample solution, and functions as first electrode 32*d*.

In FIG. 2, eighteen first electrodes 32*d* are provided. Of the first electrode body 32, the part on which the upper layer 40 is formed, i.e., a part not gray-colored without printed designation on the first electrode body 32 in FIG. 2 is not to be in contact with the sample solution. Thus, this part does not function as a first electrode. The first electrode body 32 comprises parts exposed from the upper layer through-holes 41b, the electronic signal transmission parts 32a not to be in contact with the sample solution due to coverage by the upper layer 40, and a stem 32b that connects all the electronic signal transmission parts 32a to. In addition, the first electrode body 32 has first electrode lead 32c at one end of the stem 32b.

The substrate 31 has a plurality of substrate through-holes 33. In FIG. 2, forty five substrate through-holes 33 are provided. The forty five substrate through-holes 33 are provided such that the position and the shape agree and overlap with those of forty five upper layer through-holes 41a not to allow a part of the first electrode body 32 to be exposed, of the upper layer through-holes 41. Of the upper layer through-holes 41, a part of the second electrode body 12 is exposed via the substrate through-hole 33 from the forty five upper layer through-holes 41a not to allow a part of the first electrode body 32 to be exposed. More specifically, gray-colored portions on the second electrode body 12 in FIG. 2 are brought into contact with the sample solution, and functions as second electrode 12d.

In FIG. 2, forty five second electrodes 12d are provided. Of the second electrode body 12, the part on which the substrate 31 is formed, i.e., a part not gray-colored without printed designation on the second electrode body 12 in FIG. 2 is not to be in contact with the sample solution. Thus, this part does not function as a second electrode. The second electrode body 12 comprises parts exposed from the upper layer through-holes 41a via the substrate through-holes 33, the electronic signal transmission parts 12a not to be in contact with the sample solution due to coverage by the substrate 30, and a stem 12b that connects all the electronic signal transmission parts 12a to. In addition, the second electrode body 12 has second electrode lead 12c at one end of the stem 12b.

Next, the upper layer through-holes 41 and the substrate through-holes 33 will be explained. The upper layer through-hole 41a and the substrate through-hole 33 are both penetrated in the vertical direction, and have a substantially constant cross-sectional shape and a constant area along on the plane view. The area of each upper layer through-hole 41a is substantially the same as the area of each substrate through-hole 33. The area of the first electrode 32d is the same as the area of the upper layer through-holes 41b, and the area of the second electrode 12d is the same as the area of the substrate through-hole 33. The shape is either a square or rectangle, and the area thereof may be, for example, 10 μm² to 10,000 μm². When this area is greater than 10,000 μm², an undesirable reaction as shown on the right side in FIG. 19 occurs, and consequently, problems in elevation of sensitivity may be caused. It is preferred that the areas of all the first electrodes 32d are substantially the same, and the areas of all the second electrodes 12d are substantially the same.

It is preferred that the lower layer 11 has a thickness of not less than 100 μm, in view of keeping the strength of the electrode. In addition, the substrate 31 and the upper layer 40 have a thickness of not less than 0.05 μm and not greater than 50 μm, respectively. When the substrate 31 and the upper layer 40 has a thickness of less than 0.5 μm, electrically shorting between the first electrode body 32 and the second electrode body 12 may occur due to generation of a pinhole. In addition, the generation of the pinhole results in contact of the electrode body part other than the first electrode 32d and the second electrode 12d with the sample solution. And thereby the function of the electrode plate for electrochemical measurements of the present invention may not be performed in detecting or quantifying the target substance contained in a sample solution. In addition, when the thickness is greater than 50 μm, disadvantages in forming the substrate through-holes 33 and the upper layer through-holes 41, such as a long time period for formation as well as failure in forming fine through-holes may be caused. Moreover, the interval between the first electrode 32d and the second electrode 12d may increase, and as a result, the diffusion length between the reductant and the oxidant reacted on the electrode may be increased, and sufficient redox cycle effects cannot be expected.

Figure 12:
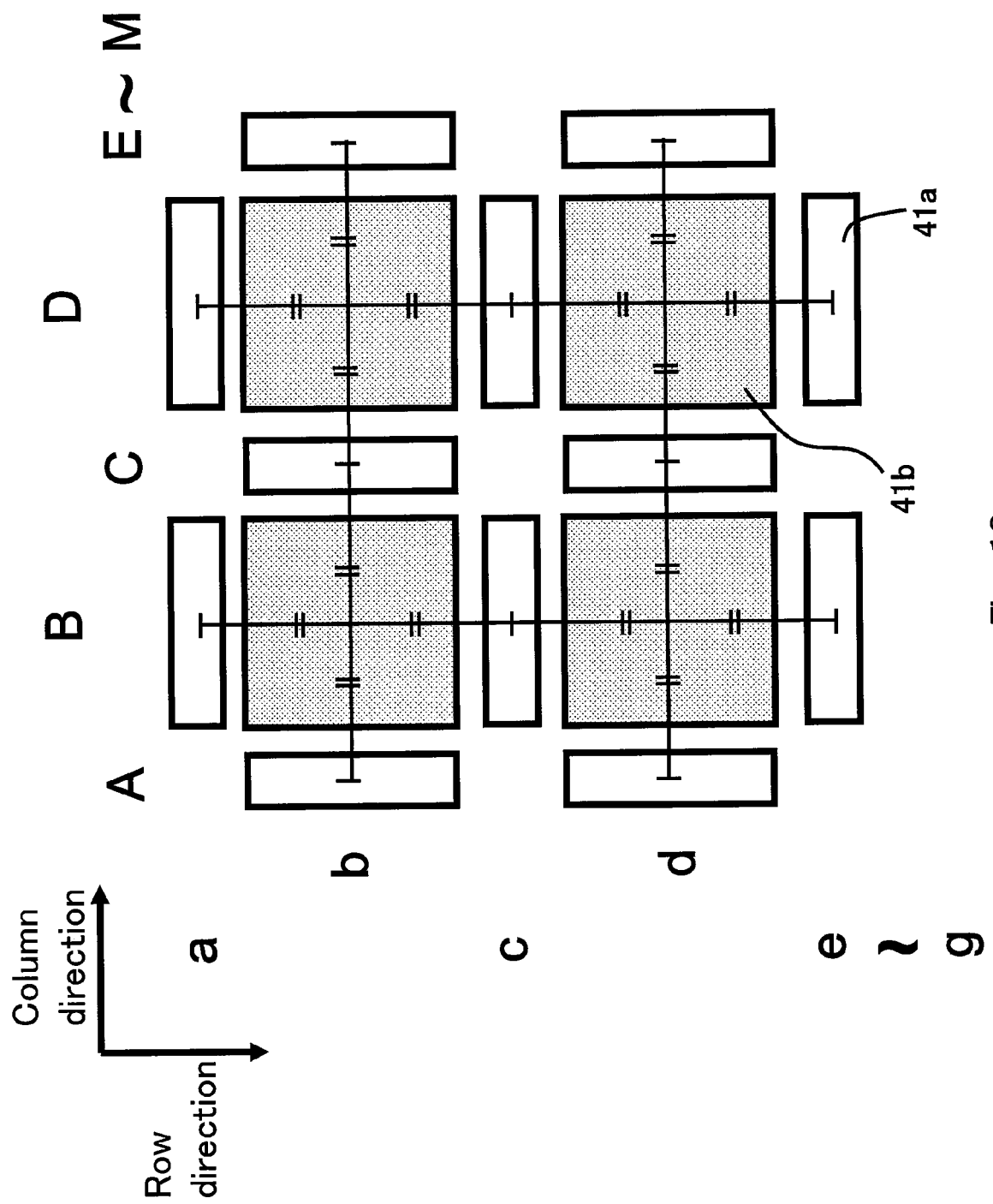
FIG. 12 shows a plane view schematically illustrating the arrangement of the upper layer through-holes of the electrode plate for electrochemical measurements of Embodiment 1.

Next, the arrangement relation between the upper layer through-holes 41a and 41b, and the areas thereof will be explained. FIG. 12 shows a plane view illustrating a part of the arrangement of the upper layer through-holes 41a and 41b on the upper layer 40. In FIG. 12, for convenience, only the upper layer through-holes 41b are gray-colored to distinguish from the upper layer through-holes 41a. In addition, straight lines are drawn between some upper layer through-holes 41b with the upper layer through-holes 41a closest thereto so as to facilitate confirmation of the positional relationship with the closest upper layer through-holes 41.

The upper layer through-holes 41b are arranged on every other positions along the row direction (B, D . . . ), and also on every other positions along the column direction (b, d . . . ). Therefore, there exists positions without the upper layer through-holes 41b being present along the row direction, i.e., columns (A, C, E, G, I, K, M). Further, there exist positions without the upper layer through-holes 41b being present along the column direction, i.e., rows (a, c, e, g). On these rows (A, C, E, G, I, K, M) and columns (a, c, e, g), the upper layer through-holes 41a are present on every other positions. Four upper layer through-holes 41a are arranged so as to surround each upper layer through-hole 41b.

The distance between the center of the upper layer through-holes 41b and the center of each of the four upper layer through-holes 41a is constant.

For example, taking note on one upper layer through-hole 41b (B, b), four upper layer through-holes 41a (B, a), (C, b), (B, c), (A, b) are arranged therearound so as to get close with an identical distance between centers. The interval is preferably 1 to 20 μm. When the interval is less than 1 μm, positioning in the manufacturing step of the electrode plate may be difficult, which may result in generation of defective products. To the contrary, when the interval is greater than 20 μm, with respect to the oxidant and reductant, the diffusion length between the first electrode 32d and the second electrode 12d shown in FIG. 19, i.e., the oxidation electrode and the reduction electrode is increased, and sufficient redox cycle effect cannot be expected.

The distances between centers of one upper layer through-holes 41b and adjacent upper layer through-holes 41a arranged along the row direction or column direction, are substantially constant. Additionally, the area of the gray-colored upper layer through-hole 41b is equal to the area of the first electrode 32d. The area of this first electrode 32d is substantially the same as the total area of the four upper layer through-holes 41a adjacent thereto along the four directions of the row direction and the column direction. More specifically, the area of one first electrode 32d is equal to total are of the adjacent four second electrodes 12d.

Again with reference to FIG. 2, the potential can be applied independently to the first electrode body 32 and the second electrode body 12, respectively, and then an electrochemical reaction, more specifically an oxidative reaction and a reductive reaction of the target substance can be progressed on each electrode. In general, an electrode on which an oxidization reaction proceed is referred to as "oxidation electrode", while an electrode on which a reduction reaction proceed is referred to as "reduction electrode".

The electric signal generated by the electrochemical reaction on the second electrode 12d is transmitted to through the second electrode body 12, and can be quantified with a measuring instrument such as a galvanometer via the second electrode lead 12c. Similarly, the electric signal generated by the electrochemical reaction on the first electrode 32d is transmitted to through the first electrode body 32, and can be quantified with a measuring instrument such as a galvanometer via the first electrode lead 32c.

The second electrodes 12d having the long side along the column direction are adjacent to two first electrodes 32d with an even distance between centers in two row directions on the plane view. The second electrodes 12d having the long side along the row direction are adjacent to two first electrodes 32d with an even distance between centers in two column directions on the plane view. Each first electrode 32d is adjacent to four second electrodes 12d with an even distance between centers in the four directions of row directions and column directions on the plane view. In other words, each electrodes 32d and 12d are adjacent to one first electrode 32d and four second electrodes 12d which can function through forming electrochemical pairs, and hence an efficient redox cycle is allowed to proceed by forming such that the area of the adjacent first electrode 32d becomes equal to total area of second electrodes 12d adjacent to the first electrode 32d.

Additionally, by finely forming the first electrodes 32d and the second electrodes 12d, respectively, functions on the electrodes can be rapidly reached to the steady state. Moreover, by forming the first electrodes 32d and the second electrodes 12d with a regular interval, uniform reaction speed can be attained on the electrode plate to prevent from generation of the concentration gradient due to the difference in the electrode reaction speed. This allows the reaction on the electrode plate to maintain the steady state. When an oxidative/reductive substance contained in a sample solution is quantified by an electrochemical method using the electrode plate for electrochemical measurements 1 according to this embodiment, the oxidative/reductive substance can be detected with superior rapidity and sensitivity by an efficient redox cycle.

Such sets of the first electrodes 32d and the second electrodes 12d arranged on the four directions therearound are preferably arranged as many as possible. By arranging the sets of the first electrodes 32d and the second electrodes 12d in a large number allows the electrode area to be in contact with the sample solution to be increased. In other words, the area of the interface between the target substance contained in the sample solution and the electrode increases to obtain a high kinetic current upon the electrochemical reaction on the electrode surface. The electrode surface area of these first electrodes 32d or second electrodes 12d is larger as the surface roughness is greater as compared with the projected area. For example, the electrode formed by a process of printing electric conductive particles, has a great surface roughness, and then the area of the electrode can be increased.

Next, the material of the member constituting the electrode plate for electrochemical measurements 1 according to this embodiment is described in detail. As the lower layer 11, a substrate having insulation properties in its entirety or on the surface thereof may be used. For example, a silicon substrate having an oxide film on which an $SiO_2$ film is coated as an insulating layer on the surface of a silicon substrate, a quartz glass plate, an aluminum oxide substrate, a substrate formed with a resin material such as a polyethylene terephthalate film, a polyethylene naphthalate film or a polyimide film can be used.

The first electrode body 32 and the second electrode body 12 are formed with a material having electrically conductive properties such as a metal, a metal oxide or a semiconductor. Examples of the material having electrically conductive properties which can be used include metals such as gold, platinum, palladium, silver, chromium, titanium and nickel, semiconductors such as p-type and n-type silicon, p-type and n-type germanium, cadmium sulfide, titanium dioxide, zinc oxide, gallium phosphide, gallium arsenide, indium phosphide, cadmium selenide, cadmium telluride, molybdenum diarsenide, tungsten selenide, copper dioxide, tin oxide, indium oxide and indium tin oxide, as well as electrically conductive carbon such as Kechen black. Gold, platinum or palladium which is stable as an electrode material is preferably used.

The substrate 31 and upper layer 40 can be formed using silicon oxide typified by $SiO_2$ or silicon nitride, with a method such as atmospheric pressure CVD, low pressure CVD, plasma CVD, or sputtering. Alternatively, they can be produced by coating a resin material such as e.g., spin-on glass (Tokyo Ohka Kogyo Co., Ltd.), a silicon resin such as Elastosil (manufactured by Asahi Kasei Wacker Silicones Corporation), polyimide or a derivative thereof such as Kapton® (manufactured by Du Pont-Toray Co., Ltd.), an epoxy resin such as JER (manufactured by Japan Epoxy Resins Co., Ltd.), a thermosetting resin such as Sumicon (manufactured by Sumitomo Bakelite Co., Ltd.), a photoresist agent or a photosensitive resin such as PMER (manufactured by Tokyo Ohka Kogyo Co., Ltd.) or SU8 (manufactured by Kayaku Microchem Co., Ltd.), by spin coating, followed by a procedure including baking, exposure with an electronic beam or an ultraviolet ray, development process in combination. In view of ease of processing in the step for forming pores described later, silicon oxide, silicon nitride, a photoresist material or a photosensitive resin may be preferably used.

Furthermore, when the electrode plate for electrochemical measurements 1 is manufactured, patterning of the conductive material is carried out so as to form the second electrode body 12 on the upper face of the lower layer 11, and the first electrode body 32 on the upper face of the substrate 31. For the patterning of the electrode, a combination method involving a film formation procedure such as vapor deposition or sputtering and an etching procedure; a procedure in which a film formation procedure is carried out with a metal mask in combination, a lift off process carried out using a photoresist, screen printing with a screen, a laser ablation process using a mask, or a direct drawing procedure by an ink jet printing process can be employed.

Formation of the upper layer 40 with a photoresist or photosensitive resin material carried out after lamination is orderly carried out on the lower layer 11 to form the first electrode body 32 is now explained. A precursor material of the photoresist is applied on the substrate 31 having the first electrode body 32 formed thereon, and then a baking step is carried out. An image mask having a pattern in which a plurality of square or rectangular pores having an equal area are arranged in the lateral direction and the lengthwise direction with an given distance between centers is overlaid thereon, and the mask pattern is exposed with an electronic beam, an ultraviolet ray, and developed to transfer the pattern to the photoresist or the photosensitive resin material on the substrate, followed by subjecting to etching to form substrate through-holes 33. Using a mask and a photosensitive resin material thereon, the upper layer 40 having upper layer through-holes 41 can be formed. Alternatively, the substrate through-holes 33 and the upper layer through-holes 41 may be formed by a lift-off process.

It is preferred that the first electrode body 32 and the second electrode body 12 be formed by the same process. For example, when the second electrode body 12 is formed by a film forming process, the first electrode body 32 is preferably formed by the film forming process. Alternatively, when the second electrode body 12 is formed by a printing process of a paste material, the first electrode body 32 is preferably formed by a similar process and with a similar material. Such a way is preferred since extreme difference in surface roughness of the first electrode body 32 and the second electrode body 12 leads to difficulty in formation of the first electrode 32d and the second electrode 12d having an approximate surface area.

According to the method for production described above, the upper layer through-holes 41a and 41b, and the substrate through-holes 33 having the shape, area and arrangement described above can be readily formed. Then coordination to give even concentrations of the reaction products yielded from the first electrode 32d and the second electrode 12d respectively can be facilitated. In addition, by coordinating to give even distance between centers of the electrode pairs of the first electrode 32d with the second electrode 12d, equal rate of the redox cycle reaction that proceeds between each of the electrode pairs can be precisely achieved. Moreover, these actions enable the electrochemical reaction to quickly attain the steady state on the first electrode 32d and on the second electrode 12d. As a result, the target substance contained in the sample solution can be detected or quantified with rapidity and favorable sensitivity.

In the electrode plate for electrochemical measurements 1 according to this embodiment, the upper layer through-hole 41 and the substrate through-hole 33 serve as a paths of the sample solution; therefore, the inner walls of the upper layer through-hole 41 and the substrate through-hole 33 are desirably hydrophilic when the sample solution is an aqueous solution. Thus, it is desired to select as the upper layer 40 and the substrate 31, a substrate having a hydrophilic surface such as a silicon substrate or a glass substrate, or a substrate constructed with a hydrophilic polyester material such as a polyethylene terephthalate or polyethylene naphthalate substrate. When a hydrophobic substrate is used, it is desired to subject the inner wall of the upper layer through-hole 41 or the substrate through-hole 33 to a hydrophilizing treatment with ethanol, isopropyl alcohol. Alternatively, it is preferable to subject to a hydrophilizing treatment by a UV ozone treatment or an oxygen plasma treatment.

Explanation of Apparatus for Electrochemical Measurements

Figure 3:
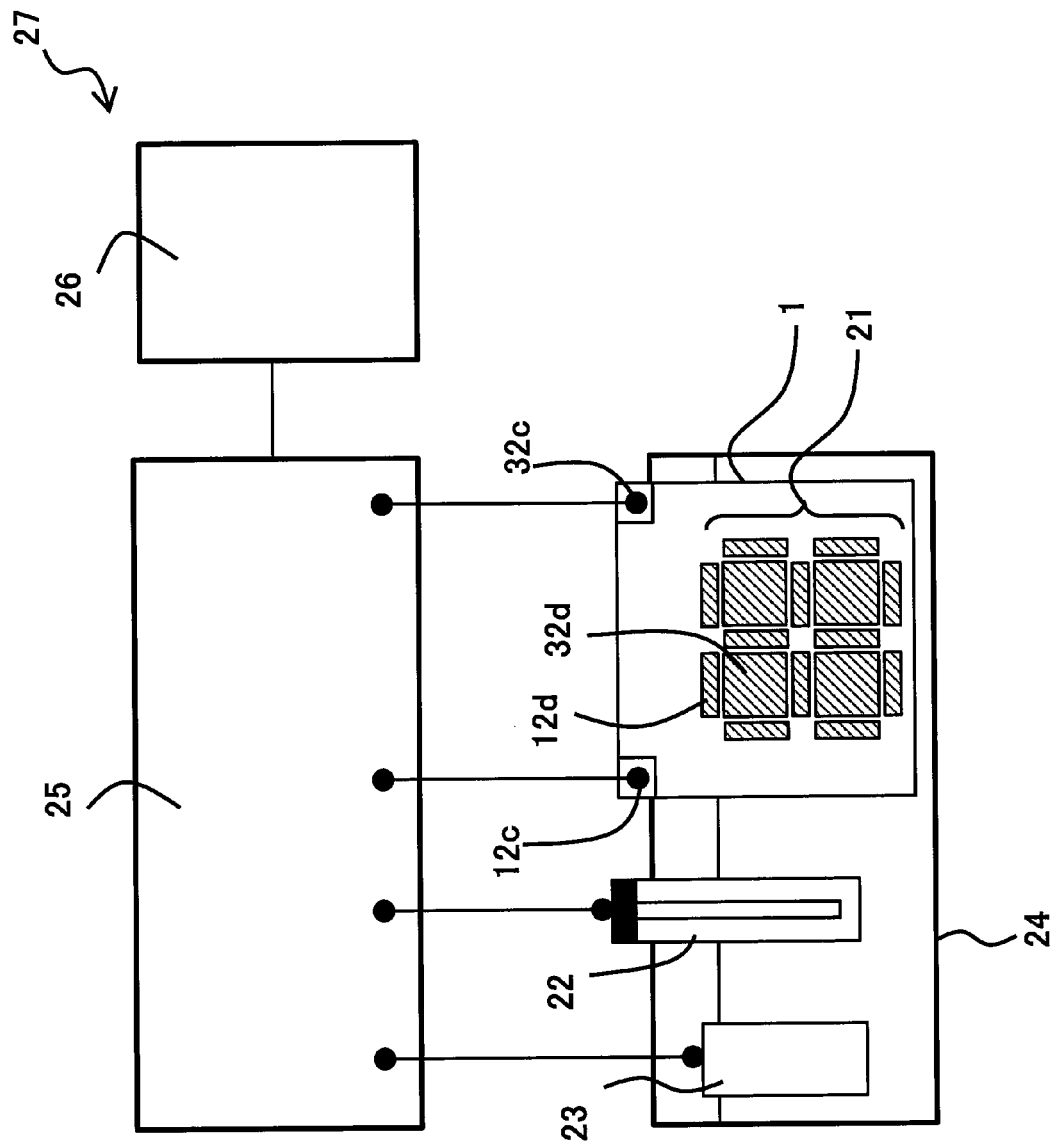
FIG. 3 shows a schematic view illustrating an apparatus for electrochemical measurements comprising an electrode plate for electrochemical measurements according to Embodiment 1.

FIG. 3 shows an apparatus for electrochemical measurements having an electrode plate for electrochemical measurements (hereinafter, may be merely referred to as "measurement apparatus") according to Embodiment 1.

As shown in FIG. 3, the electrode plate for electrochemical measurements 1, reference electrode 22, and auxiliary electrode 23 are immersed in a sample solution filled in sample vessel 24 in measurement apparatus 27. Accordingly, these electrodes are brought into contact with the sample solution. In addition, a plural number of first electrodes 32d and second electrodes 12d are formed in the row direction and the column direction on the surface of the electrode plate for electrochemical measurements 1 to form the electrode assembly 21.

The reference electrode 22 is an electrode that serves in representing a standard of the potential applied to the electrode plate for electrochemical measurements 1. The potential shown by the reference electrode 22 in the sample solution is defined as zero, and the potentials are applied to the first electrode 32d and the second electrode 12d, respectively. The auxiliary electrode 23 is an electrode for compensating the electric current so as to conform to Ampere's law in the measurement apparatus 27. The control unit 25 is electrically connected to the electrode plate for electrochemical measurements 1 via the first electrode lead 32c and second electrode lead 12c, and also, electrically connected to the reference electrode 22 and the auxiliary electrode 23. The electric current response that is output from the control unit 25 is recorded by recorder 26.

Explanation of Electrochemical Measuring Method

Next, a method for quantifying the electronic mediator contained in a sample solution is explained with reference to FIG. 3.

According to a process such as cyclic voltammetry, the potential to allow the oxidative reaction to proceed, and the potential to allow the reductive reaction to proceed in the electronic mediator are determined beforehand, and used for the potential value of the oxidation electrode and the potential value of the reduction electrode described later. The standard of the potential is an equilibrium potential represented by the reference electrode 22 in the sample solution. In other words, the potentials applied to the second electrode 12d and the first electrode 32d, respectively, are a relative potential defined for the reference electrode 22 as 0 V. After the potentials of the second electrode 12d and the first electrode 32d are entered into the control unit 25, the measurement is started. Although explained in detail in Examples described later, the case in which the first electrode 32d is used as an oxidation electrode, while the second electrode 12d is used as the reduction electrode is now described as one example. In other words, an oxidation reaction proceeds on the first electrode 32d, while a reduction reaction proceeds on the second electrode 12d in the present Embodiment.

Specific method will be explained in the following. First, a positive voltage is slowly applied from 0 V to the first electrode 32d. In Examples described later, the voltage applied to the first electrode 32d is altered slowly from 0 V to +0.7 V, and thus the first electrode 32d is used as an oxidation electrode. Such application is referred to as "sweeping". That is, the term "sweeping" used herein means to alter the potential continuously. In contrast, the term "applying" used herein means to alter a predetermined potential rapidly.

In this procedure, it is preferred to keep applying a previously determined potential that permits a reduction reaction of the electronic mediator to proceed (for example, in the case of potassium ferricyanide, 0 V on silver-silver chloride electrode) to the reduction electrode. The speed of applying the voltage (hereinafter, may be also referred to as "sweeping speed") to the first electrode 32d is generally 5 mV/sec or greater and 500 mV/sec or less. In Examples described later, the speed is 100 mV/sec.

In the foregoing description, a positive potential is swept to the first electrode 32d, while a negative potential is applied to the second electrode 12d. However, a positive potential may be applied to the first electrode 32d, while a negative potential may be swept to the second electrode 12d.

The electric current obtained by an oxidative reaction on the first electrode 32d is detected by control unit 25 via the first electrode lead 32c. Similarly, the electric current obtained by a reductive reaction on the second electrode 12d is detected by control unit 25 via the second electrode lead 12c. Thus detected electric current is output to the recorder 26, and thus the substance to be quantified in the sample solution can be quantified by comparing the recorded oxidation current with a result of measurement (calibration curve described later) of the oxidation current values of a standard sample. It is also possible to quantify the substance to be detected in the sample solution by comparing the reduction electric current value recorded on the recorder 26 with a result of measurement of the reduction electric current of a standard sample. For this purpose, it is desirable to produce a calibration curve of the standard sample beforehand using a detection device of this Embodiment.

Detection of the electric current obtained by the reduction reaction with the control unit 25 via the second electrode lead 12c enables detection not intending to quantify the substance to be detected.

Figure 4:
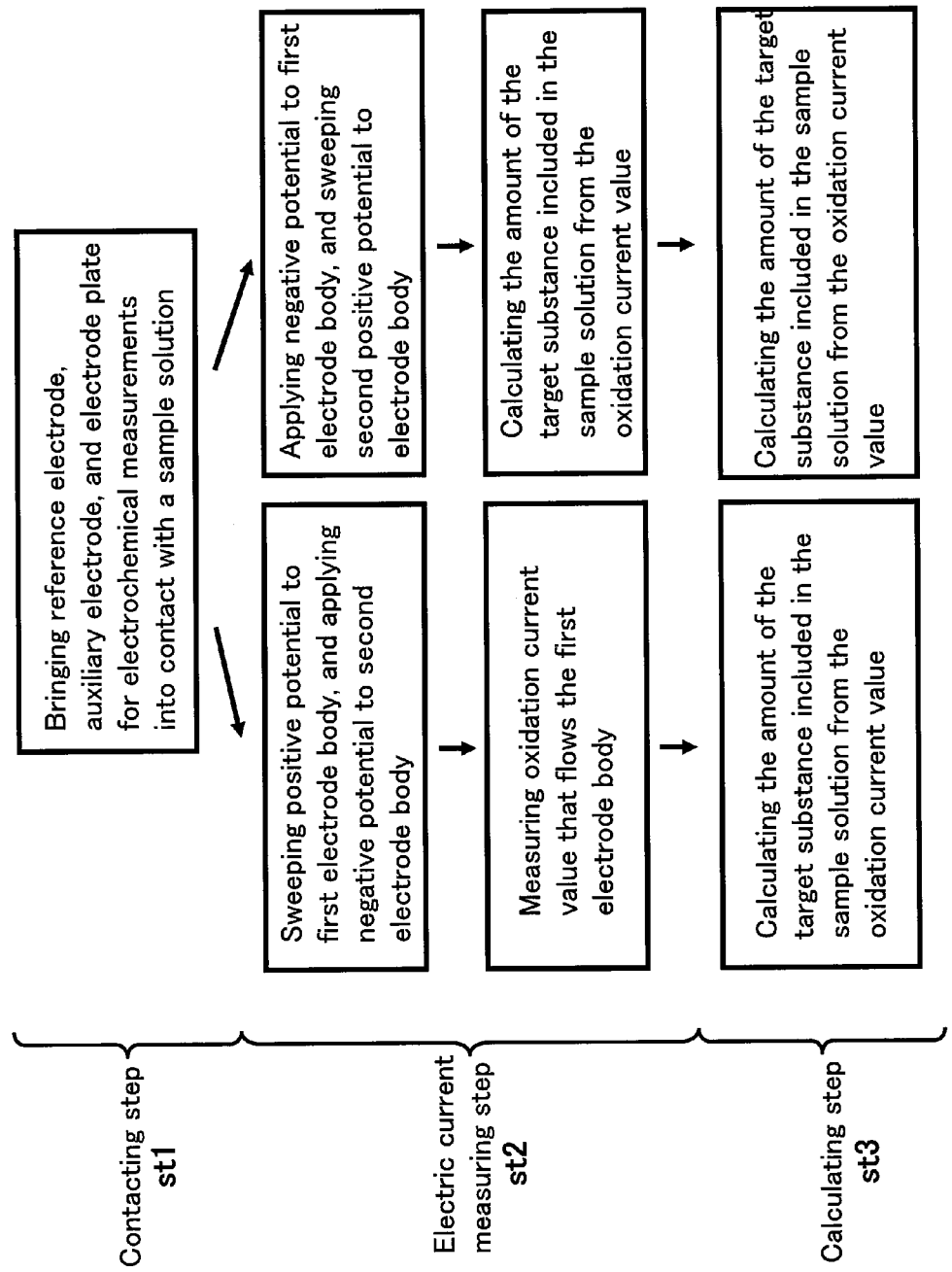
FIG. 4 shows a flowchart of steps for illustrating a process for calculating the concentration of a target substance contained in a sample solution with the apparatus for electrochemical measurements according to Embodiment 1.

A method for quantifying the substance to be detected in a sample solution using a calibration curve, i.e., a method of calculating the concentration of the substance to be detected in the sample solution is explained below. FIG. 4 shows a flow chart of steps of a process for calculating the concentration of a target substance contained in a sample solution. This process comprises, as shown in FIG. 4, contacting step of bringing the reference electrode, the auxiliary electrode, and the electrode plate for electrochemical measurements into contact with the sample solution (st1), electric current measuring step by sweeping or applying a potential to each electrode body to determine the electric current value (st2), and calculation step of calculating the concentration of the target substance contained in the sample solution based on the electric current value (st3).

In this method, a calibration curve is first produced using a standard sample. This standard sample contains a reduced electronic mediator (herein, assumed as potassium ferrocyanide) having a known concentration. Using such a standard sample having a known electronic mediator concentration as a sample solution having a known concentration, relationship between the concentration of the reduced electronic mediator, and the kinetic current value measured with the apparatus for electrochemical measurements is indicated on a graph by means of the apparatus for electrochemical measurements as illustrated in FIG. 3 according to the step flow shown in FIG. 4. One example of this graph is shown in FIG. 5.

Figure 5:
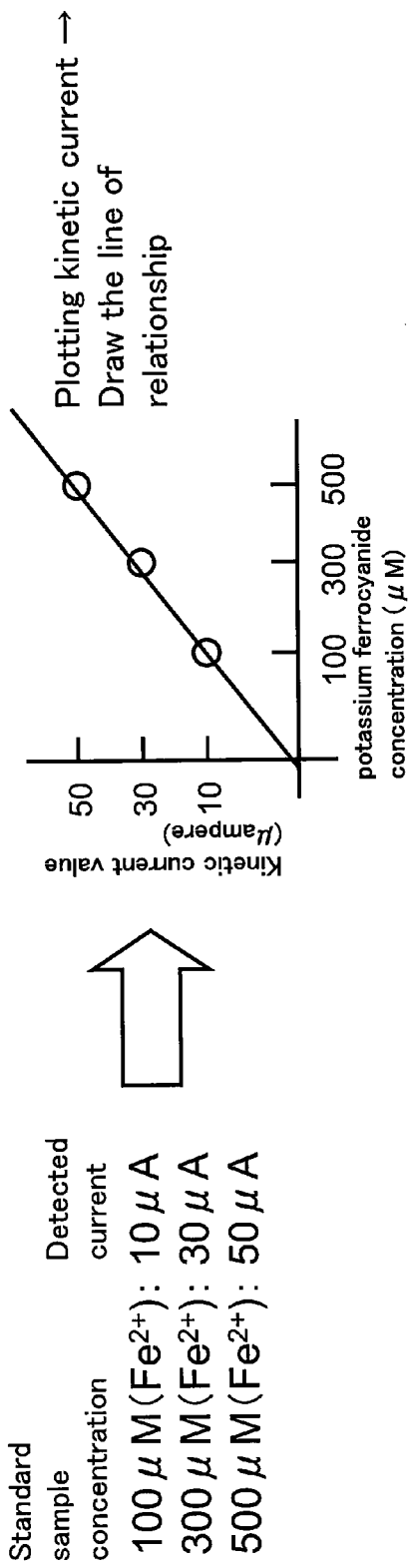
FIG. 5 shows a view illustrating one example of a process for producing a calibration curve.
Figure 5:
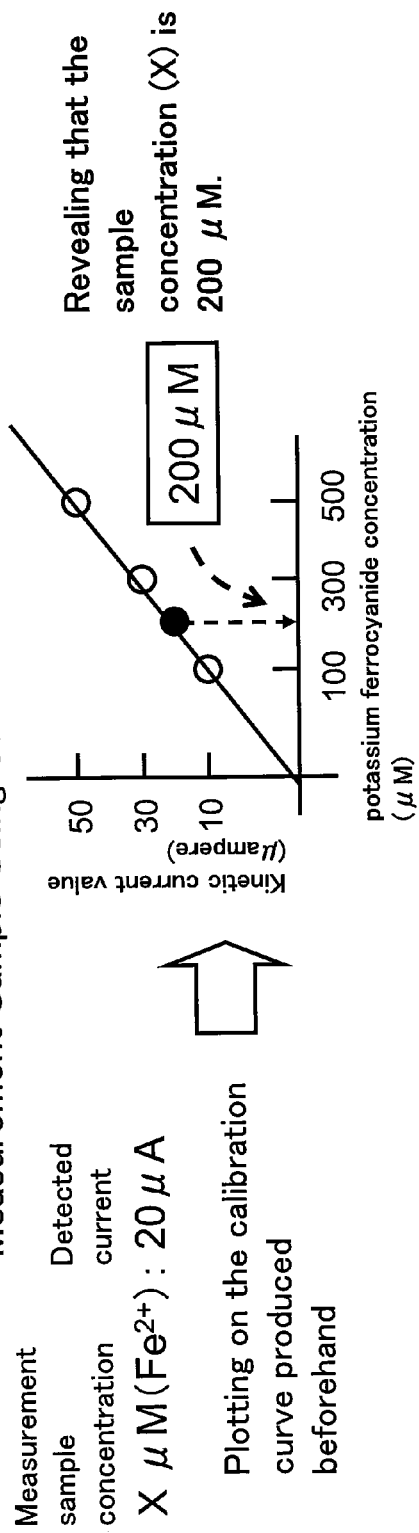

As shown in FIG. 5, it is assumed herein that: the kinetic current value is 10 μA when the concentration of the reduced electronic mediator is 100 μM; kinetic current value is 30 μA when the concentration of the reduced electronic mediator is 300 μM; and the kinetic current value is 50 μA when the concentration of the reduced electronic mediator is 500 μM. These data are plotted on a graph to draw a calibration curve. Accordingly, a calibration curve is obtained from a standard sample having a known concentration.

Next, using a sample solution the concentration of which is unknown, and the apparatus for electrochemical measurements as illustrated in FIG. 3, a kinetic current value is obtained according to the step flow shown in FIG. 4. When the kinetic current value obtained in this procedure is 20 μA, the concentration of the reduced electronic mediator contained in the sample solution can be revealed from the calibration curve. The amount of the target substance which is/was contained in the sample solution is calculated based on this concentration of the reduced electronic mediator.

It would not be necessary to mention that production of the calibration curve, calculation of the amount of the target substance, may be all carried out on a computer, in effect.

Explanation of Reference Electrode, and Auxiliary Electrode

Again with reference to FIG. 3, it is also possible to carry out the measurement using one counter electrode in place of the two electrodes, i.e., the reference electrode 22 and the auxiliary electrode 23 shown in FIG. 3. However, it is preferred to provide the reference electrode 22 and the auxiliary electrode 23 independently because the electrode reaction proceeds on the surface while the electric current flows to the counter electrode or the reference electrode to be a standard of the potential. And the potential employed as a standard of the detection device of this Embodiment varies when alteration of the concentration of the electronic mediator is enhanced as the reaction proceeds, whereby accurate measurement cannot be executed.

Therefore, it is desirable to preset the input impedance as large as possible so as to prevent the electric current from flowing to the reference electrode 22. Desirably, the impedance value is set to be equal to or greater than $10^6$ ohm. A silver-silver chloride electrode, a saturated calomel electrode can be used for the reference electrode 22.

It is desired that the auxiliary electrode 23 has a large surface area. Preferred surface area of the auxiliary electrode 23 is ten times larger than that of the assembly 21 of the electrode because when sufficient electric current cannot be flowed due to too small electrode surface area of the auxiliary electrode 23, the electric current obtained with the electrode plate for electrochemical measurements 1 does not flow enough to the control unit 25, whereby an accurate electric current value is not yielded. And additionally, the potential of the auxiliary electrode 23 greatly varies for allowing the electric current to flow to lead to undesirable reactions such as electrolysis of water may be proceeded.

It is desired that a noble metal electrode that is less likely to cause an oxidation-reduction reaction of the electrode per se or a corrosion reaction is used as the auxiliary electrode 23. For example, platinum electrodes are preferred which are produced by depositing platinum black on a platinum wire to provide a great electrode area.

Figure 6:
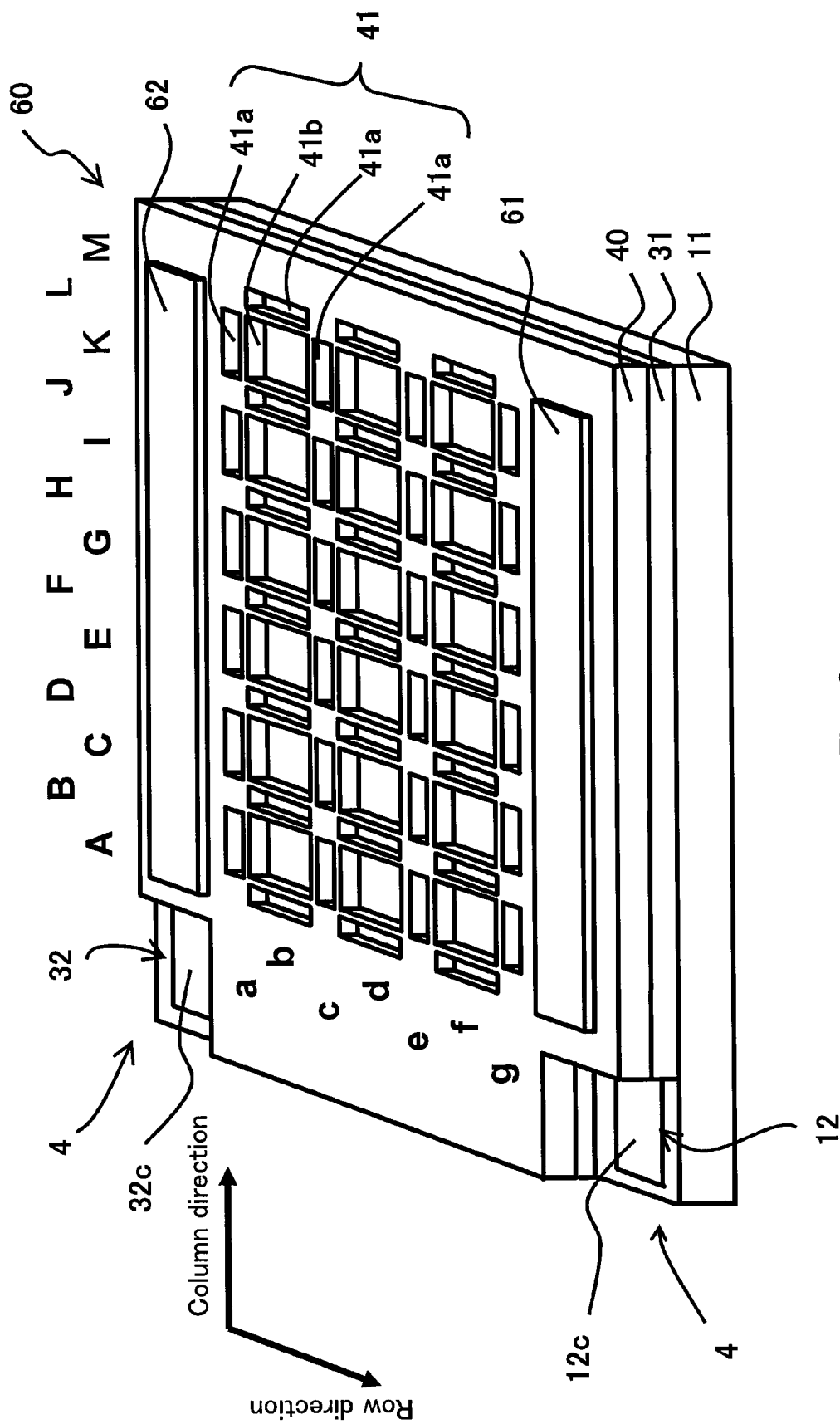
FIG. 6 shows a perspective view schematically illustrating an electrode plate in which a reference electrode and an auxiliary electrode are formed on the electrode plate for electrochemical measurements according to Embodiment 1.

FIG. 6 shows an electrode plate that constructs a measurement apparatus distinct from the apparatus for electrochemical measurements shown in FIG. 3. In the electrode plate for electrochemical measurements 60 shown in FIG. 6, reference electrode 61 and auxiliary electrode 62 are formed integrally with the electrode plate for electrochemical measurements 1 according to Embodiment 1. The reference electrode 61 and the auxiliary electrode 62 are formed on the upper layer 40. More specifically, a resist is applied on the surface of the electrode plate for electrochemical measurements 1 according to Embodiment 1, and after an image mask having a pattern of the reference electrode and the counter electrode is overlaid thereon, the pattern is exposed with an ultraviolet ray or an electronic beam, followed by development to transfer the pattern to the resist on the substrate. Thereafter, the electrode layer is formed by a procedure such as sputtering, vapor deposition, CVD, screen printing or ink printing, followed by production of the reference electrode 61 and the auxiliary electrode 62 by a lift off process for detaching the resist. Accordingly, the electrode plate 60 in which the second electrode body 12 and first electrode body 32 for serving as a working electrode body (thus referred to in general, to mention an oxidation electrode body and a reduction electrode body in combination, and herein, the combination of the first electrode body 32 and the second electrode body 12), the reference electrode 61, and the auxiliary electrode 62 are integrated can be obtained. Alternatively, the reference electrode 61, and the auxiliary electrode 62 may be also formed using a metal mask. In this case, for producing the reference electrode 61, one electrode other than the working electrode body is selected, and a metal or an organic oxidation-reduction polymer to be an indicator is provided thereon by a plating, electrolytic polymerization, or printing process. In addition, as the indicator for providing on the reference electrode 61, silver, silver chloride, polyvinylferrocene may be exemplified.

In the case of the electrode plate for electrochemical measurements 60, three electrodes (electrode bodies), i.e., working electrode body, reference electrode and counter electrode are formed within a single plate-like electrode plate for electrochemical measurements 60, therefore, the apparatus for electrochemical measurements constructed using the same is suitable for the measurement of small samples and in trace concentration regions, and particularly suitable for analyses of biological samples.

Embodiment 2

Figure 7:
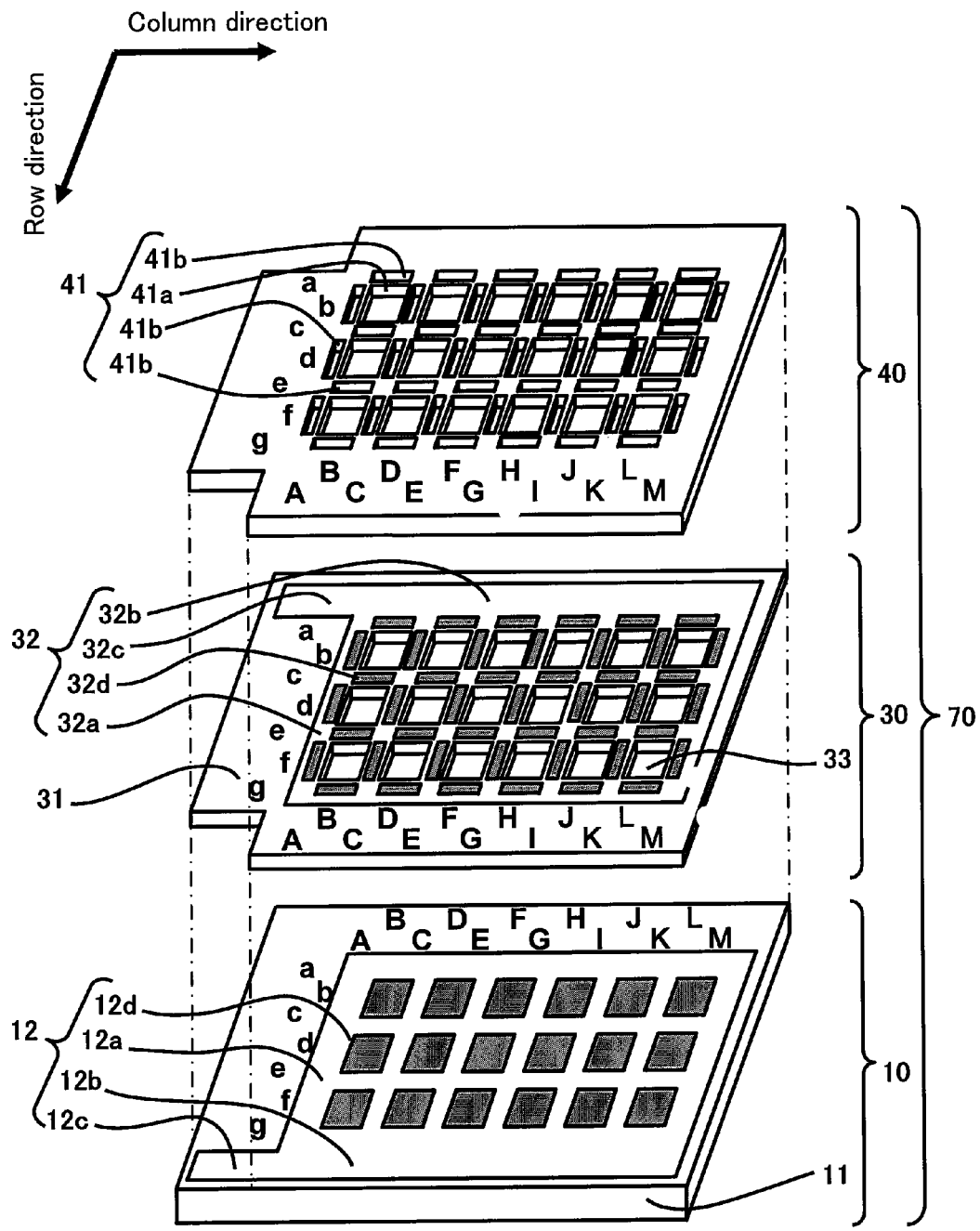
FIG. 7 shows an exploded perspective view schematically illustrating an electrode plate for electrochemical measurements according to Embodiment 2.

FIG. 7 shows an exploded perspective view schematically illustrating the electrode plate for electrochemical measurements according to Embodiment 2. The electrode plate for electrochemical measurements 70 according to the present embodiment is identical to that of Embodiment 1 shown in FIG. 1 on the perspective view, but is different in the shape and arrangement of both the second electrodes 12d and the first electrodes 32d. Only such differences from Embodiment 1 will be explained below.

In the electrode plate for electrochemical measurements 10 of Embodiment 1 shown in FIG. 2, the upper layer through-holes 41a to allow the second electrode 12d to be exposed are rectangular, and had a construction smaller than the square upper layer through-holes 41b to allow the first electrode 32d to be exposed in the upper layer 40, but inverse relationship is established according to the present embodiment. That is, in the present embodiment, the upper layer through-holes 41a to allow the second electrode 12d to be exposed are square, and has a construction greater than the rectangular upper layer through-holes 41b to allow the first electrode 32d to be exposed. Also, with respect to the arrangement, four upper layer through-holes 41a are arranged around one upper layer through-holes 41b in Embodiment 1 as shown in FIG. 12, while four upper layer through-holes 41b are arranged around one upper layer through-holes 41a in the present Embodiment.

In FIG. 7, the first electrode 32d and the second electrode 12d are filled with gray color. As in the foregoing, the arrangement and shape of the first electrode 32d and the second electrode 12d on the plane view are counterchanged in the present Embodiment from Embodiment 1.

Since the electrode plate for electrochemical measurements 70 according to the present embodiment has a construction as described above, equivalent effects to those of the electrode plate for electrochemical measurements 1 according to Embodiment 1 can be achieved by making the exposed area of each second electrode 12d equal to total area of the first electrodes 32d therearound. Thus, when the concentration of electronic mediators in a sample solution is quantified by an electrochemical method using the electrode plate for electrochemical measurements 70 according to this embodiment, the concentration of electronic mediators can be quantified with superior accuracy by an efficient redox cycle.

Embodiment 3

Figure 8:
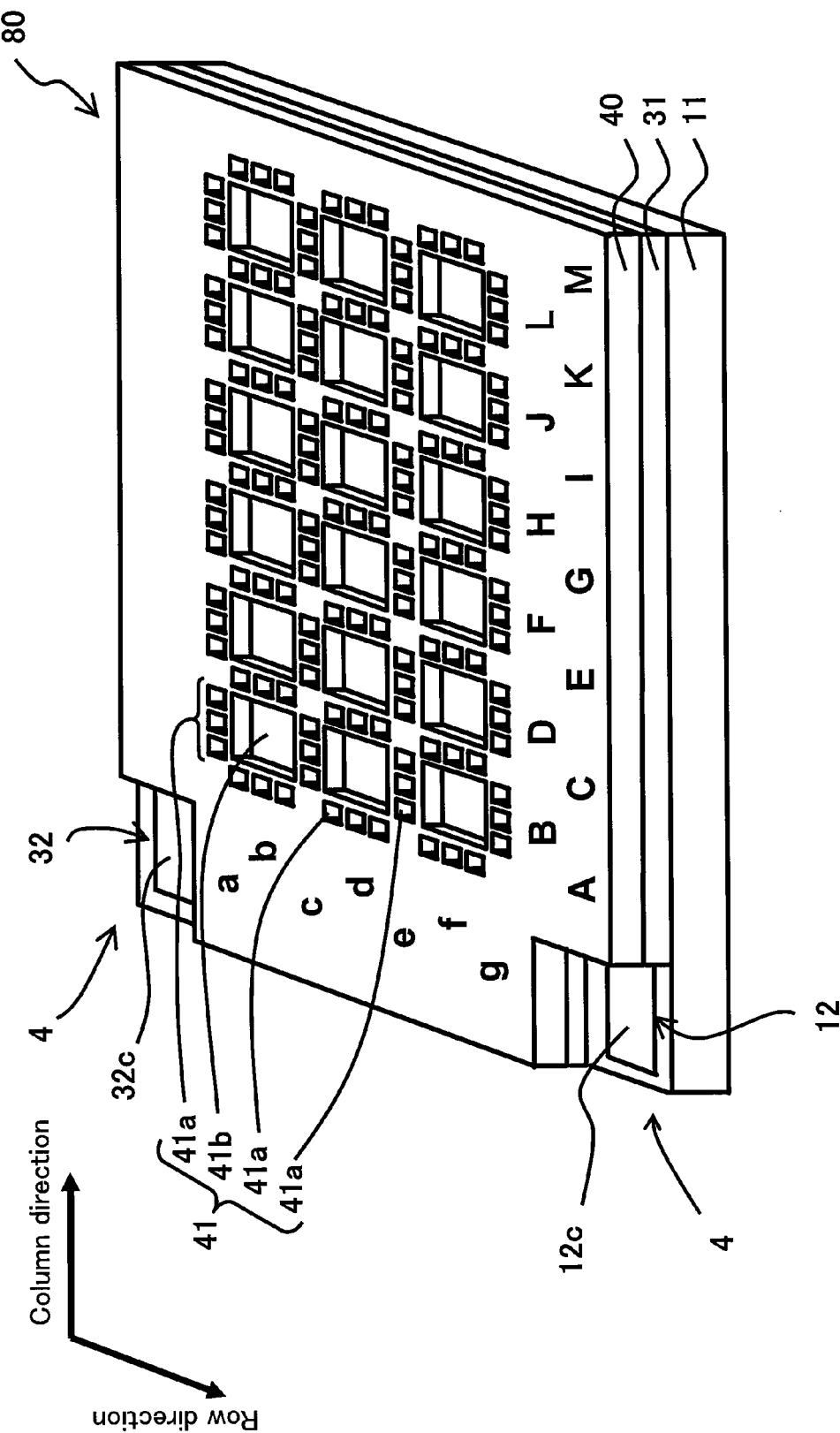
FIG. 8 shows a perspective view schematically illustrating the electrode plate for electrochemical measurements according to Embodiment 3.
Figure 9:
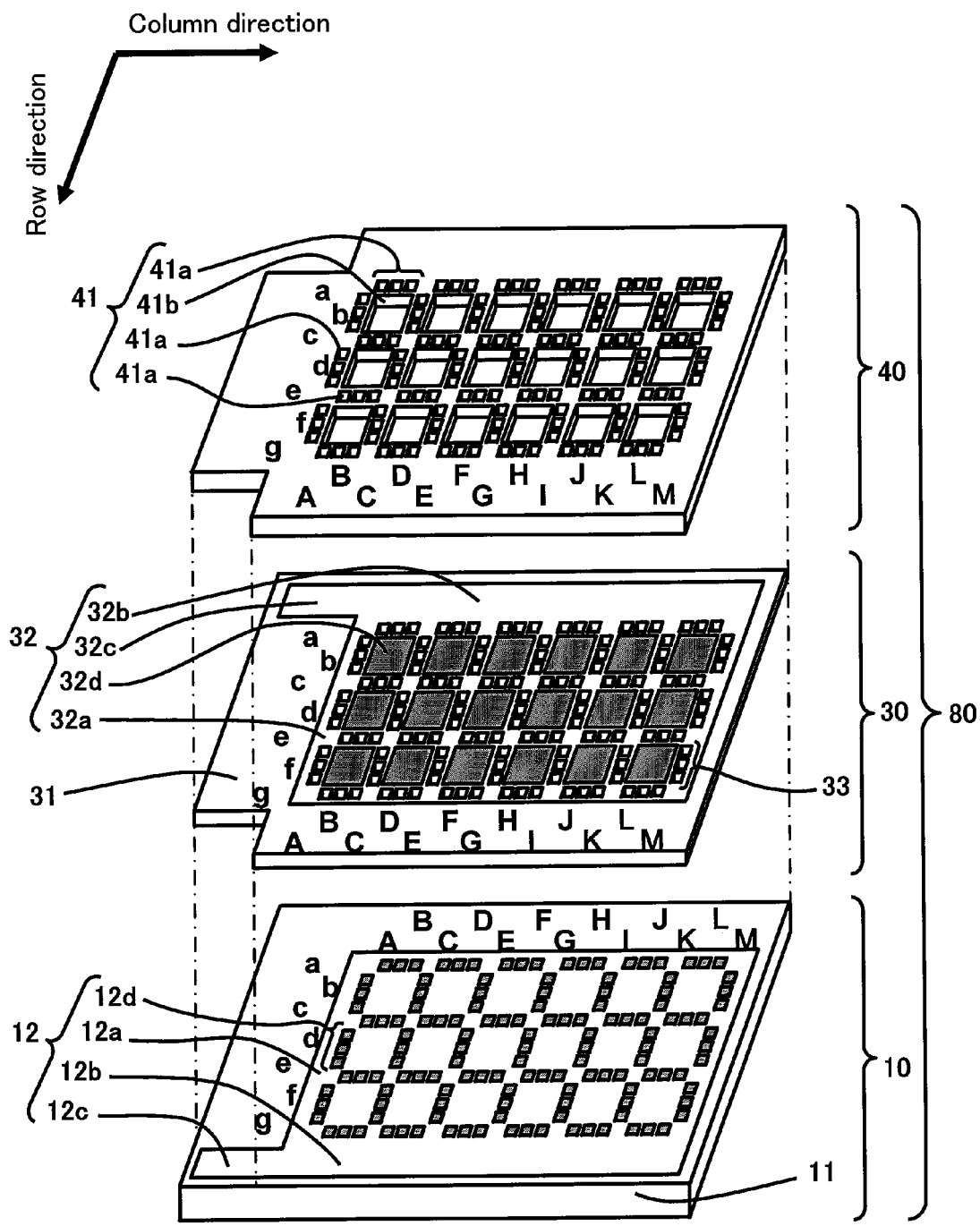
FIG. 9 shows an exploded perspective view schematically illustrating the electrode plate for electrochemical measurements according to Embodiment 3.

FIG. 8 shows a perspective view schematically illustrating the electrode plate for electrochemical measurements 80 according to Embodiment 3, and FIG. 9 shows an exploded perspective view of the same. The electrode plate for electrochemical measurements 80 of the present Embodiment is different from the electrode plate for electrochemical measurements 1 of Embodiment 1 in that each upper layer through-holes 41a is three-divided, and also the substrate through-holes 33 and the second electrode 12d are three-divided, respectively to meet therewith. Herein, each of the three-divided parts of the upper layer through-holes 41a, the substrate through-holes 33, and the second electrode 12d are fit, respectively, and then each one upper layer through-holes 41a, substrate through-hole 33 and second electrode 12d is formed.

Figure 13:
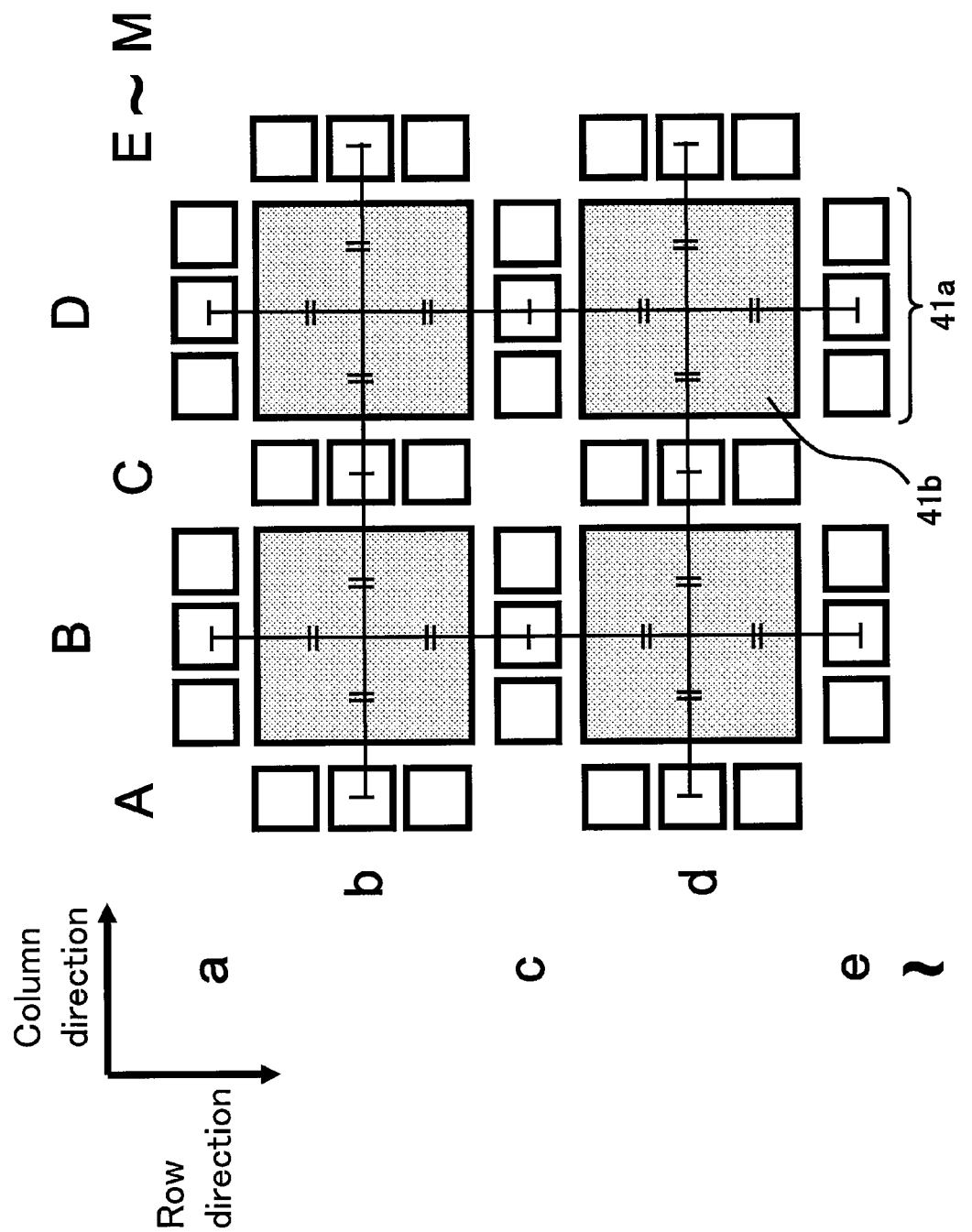
FIG. 13 shows a plane view schematically illustrating the arrangement of the upper layer through-holes of the electrode plate for electrochemical measurements of Embodiment 3.

FIG. 13 shows a top view illustrating a part of arrangement of the upper layer through-holes 41a and 41b in the upper layer 40. In FIG. 13, for the sake of expedience, only the upper layer through-holes 41b are gray-colored, which are distinguished from the upper layer through-holes 41a. Moreover, straight lines are drawn in between the upper layer through-holes 41a positioned closest to the upper layer through-holes 41b, and then confirmation of the positional relationship of the upper layer through-holes 41b with the upper layer through-holes 41a can be facilitated. In the present Embodiment, four upper layer through-holes 41a which are each three-divided are arranged around one upper layer through-hole 41b. Also in the present Embodiment, the area of the one upper layer through-holes 41b, and total area of the upper layer through-holes 41a therearound are substantially the same.

Again with reference to FIG. 9, the upper layer through-holes 41b allow the first electrode 32d to be exposed from the upper layer 40, and the upper layer through-holes 41a allow the second electrode 12d to be exposed from the upper layer 40 together with the substrate through-holes 33 having the same shape with the upper layer through-holes 41a. Thus, the electrode pairs can be formed with the first electrode 32d and the second electrode 12d closest thereto having an equal electrode also in the present Embodiment. Therefore, also in the electrode plate for electrochemical measurements 80 of this embodiment, equivalent effects to those of the electrode plate for electrochemical measurements 1 of Embodiment 1 can be achieved. Thus, when the concentration of electronic mediators in a sample solution is quantified by an electrochemical method using the electrode plate for electrochemical measurements 80 of the present embodiment, the concentration of electronic mediators can be quantified with superior accuracy by an efficient redox cycle.

Figure 10:
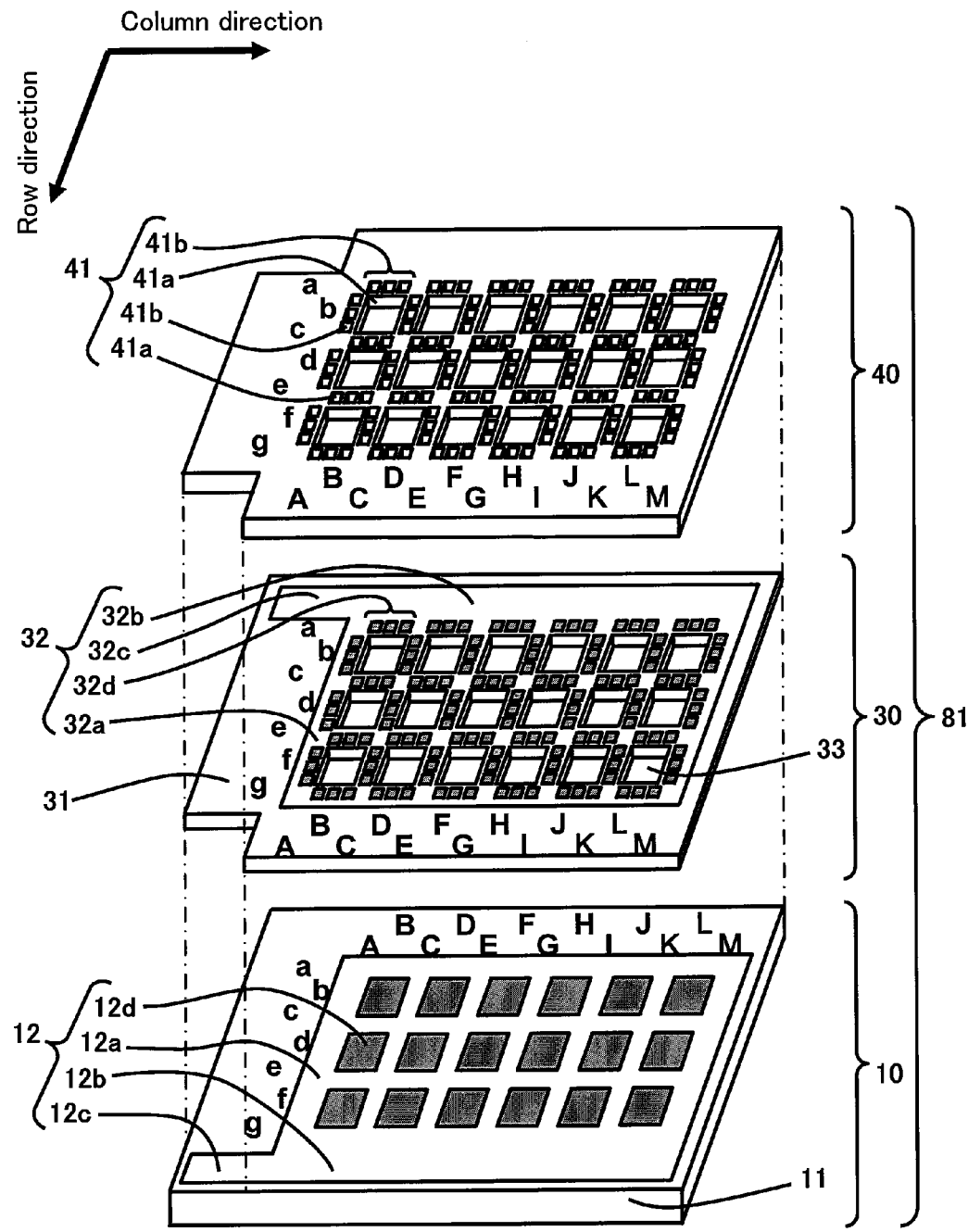
FIG. 10 shows an exploded perspective view schematically illustrating the electrode plate for electrochemical measurements according to Embodiment 4.

In a similar correlation of Embodiments 1 and 2, the shape and arrangement of the first electrode 32b and the second electrode 12b are counterchanged also in the present Embodiment as shown in FIG. 10. Accordingly, an electrode plate for electrochemical measurements 81 including upper layer through-holes 41a and 41b, and substrate through-holes 33 having different shapes may be also manufactured.

Figure 11:
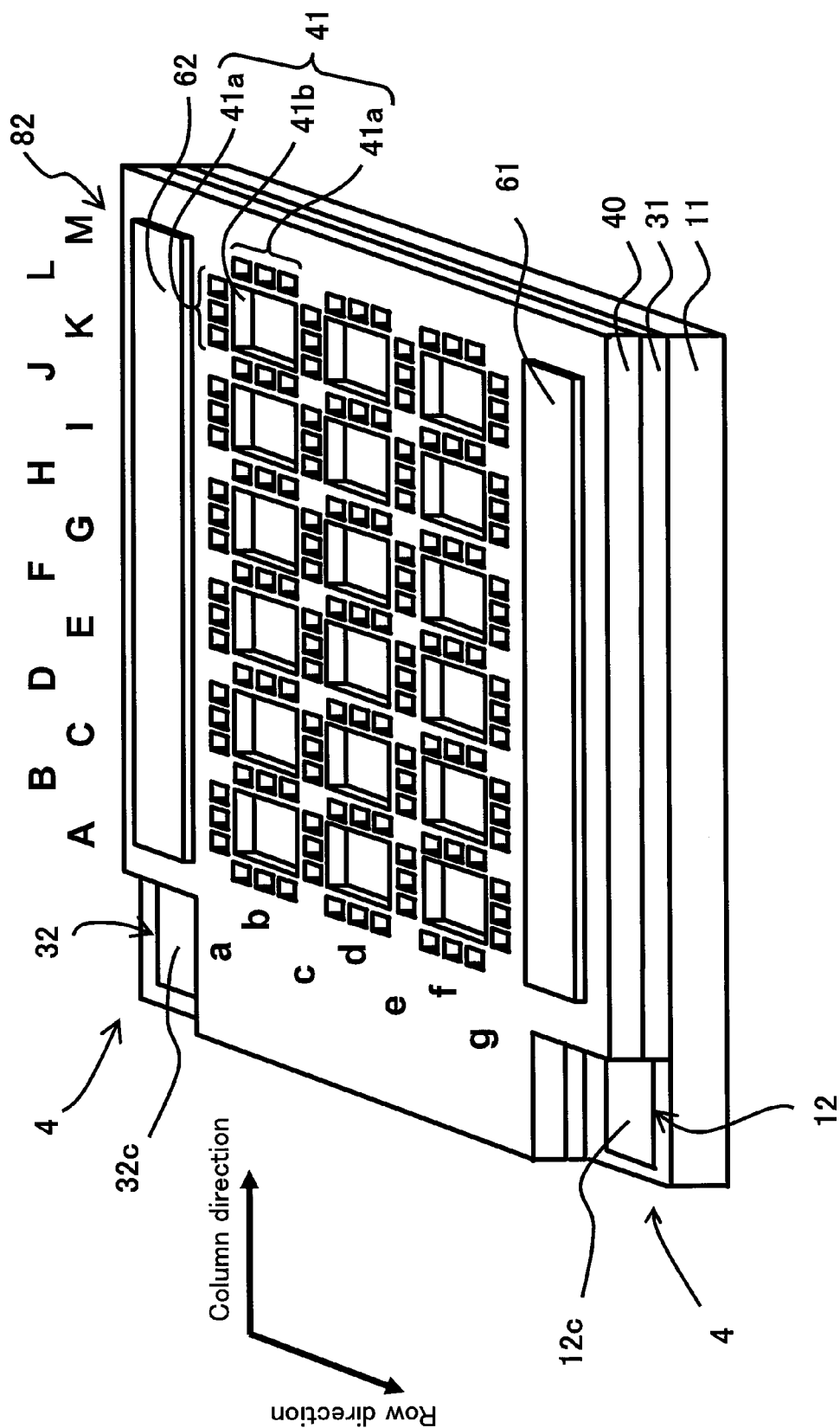
FIG. 11 shows a perspective view schematically illustrating the electrode plate in which the reference electrode and the auxiliary electrode are formed on the electrode plate for electrochemical measurements of Embodiment 3.

In addition, an electrode plate for electrochemical measurements 82 shown in FIG. 11 comprises an electrode plate for electrochemical measurements 80 with which a reference electrode 61 and an auxiliary electrode 62 are integrally formed. The apparatus for electrochemical measurements constructed using the same is suitable for measuring a slight amount of a sample, or in a trace concentration region, and can be suitably used in analyses of biological samples.

Embodiment 4

Figure 14:
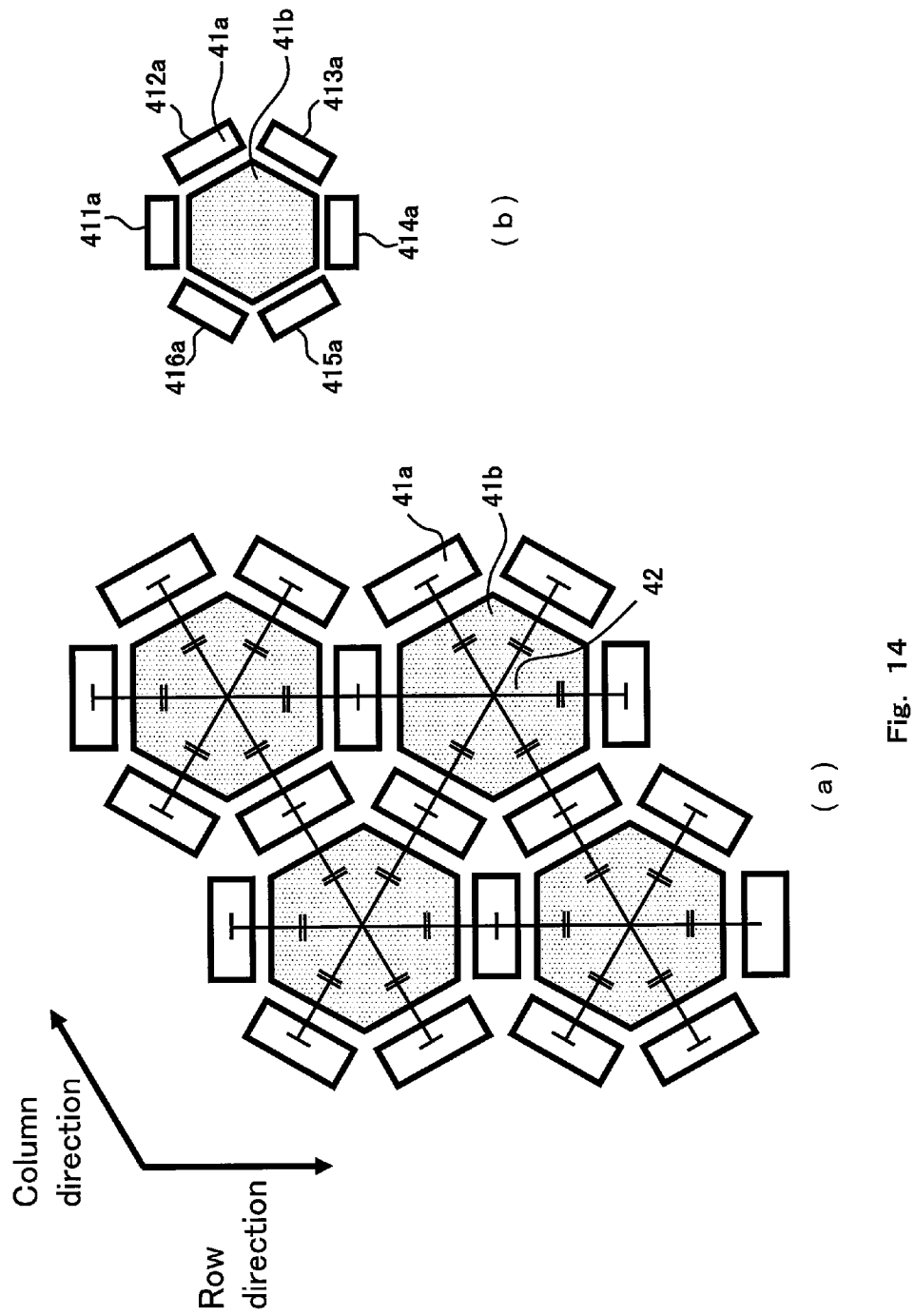
FIGS. 14(*a*) and 14(*b*) show a plane view schematically illustrating the arrangement of the upper layer through-holes of the electrode plate for electrochemical measurements of Embodiment 4

In Embodiment 4, difference from the first electrode plate for electrochemical measurements 1 lies in the shape and arrangement of the upper layer through-holes 41a and 41b. FIG. 14(*a*) shows a view schematically illustrating a part of the upper layer of the electrode plate for electrochemical measurements (not shown in the Figure) of the present Embodiment. The electrode plate for electrochemical measurements of the present Embodiment is different from the electrode plate for electrochemical measurements 1 of Embodiment 1 in that the shape of the upper layer through-holes 41b formed on the upper layer 40 is not square but regular hexagonal. In addition, the upper layer through-holes 41a are rectangular having the length of one side of being substantially the same as the length of one side of the upper layer through-holes 41b, and six upper layer through-holes 41a are arranged around each upper layer through-holes 41b with a regular interval.

FIG. 14(b) shows an electrode pair composed of one upper layer through-hole 41b and six upper layer through-holes 41a. Six upper layer through-holes 411a, 412a, 413a, 414a, 415a and 416a are arranged around the upper layer through-holes 41b with a regular interval. In addition, the area of each upper layer through-holes 41b is the same as total area of the six upper layer through-holes 41a arranged therearound. That is, the area of one first electrode is equal to the total are of the six second electrodes arranged therearound. It is preferred that the areas of all the first electrodes are substantially the same, and the areas of all the second electrodes also are substantially the same.

Also in the present Embodiment, similar effects to those in Embodiment 1 are achieved. Of course, in the present Embodiment, the manufacturing method of the electrode plate for electrochemical measurements of Embodiments 1 to 3 may be employed by appropriately arranging the electrodes.

In the following Embodiments a covering insulator which is useful in adjusting the relationship between the oxidation electrode and the reduction electrode is formed on the first electrode body or the second electrode body.

Embodiment 5

Figure 20:
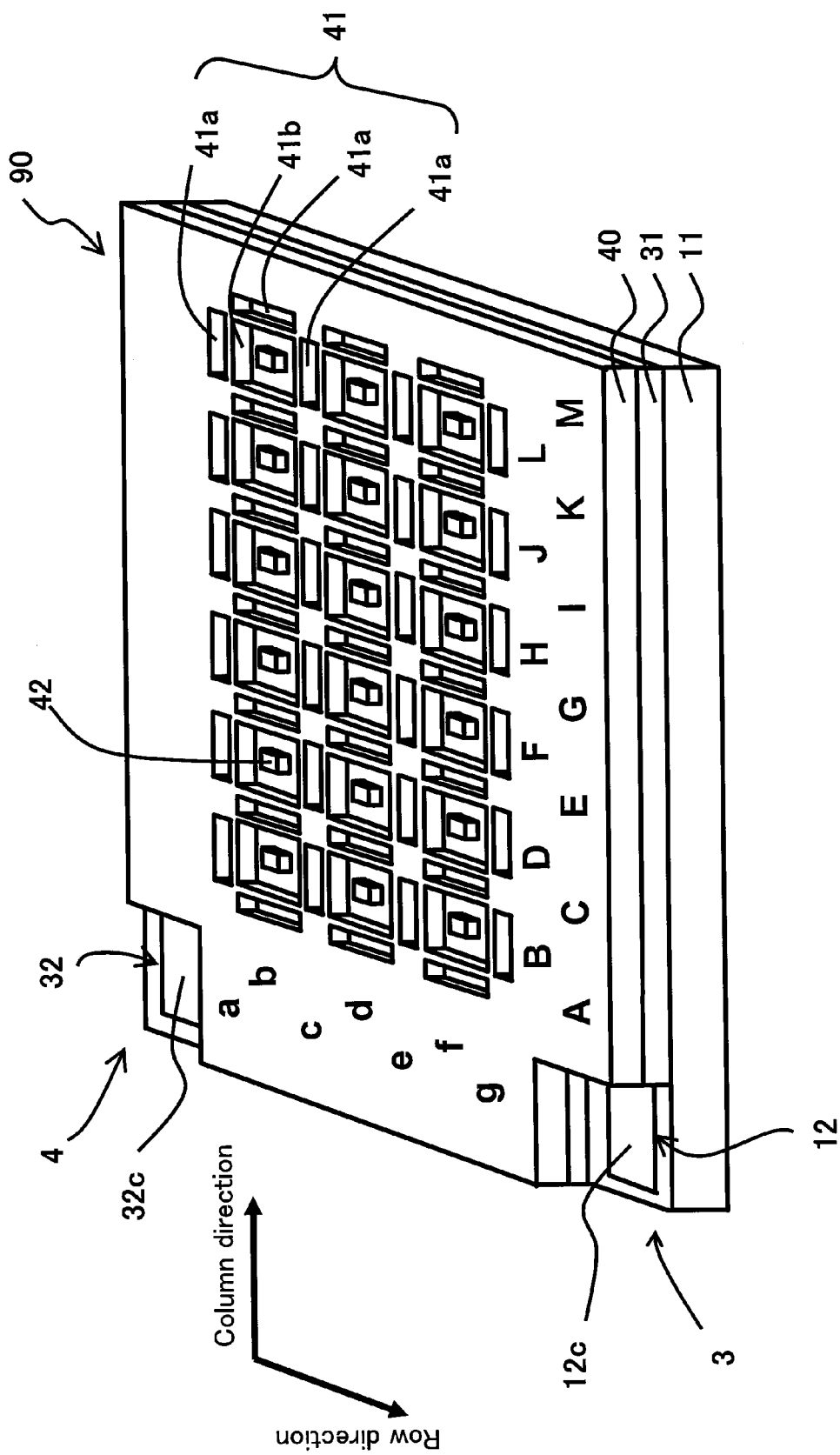
FIG. 20 shows a perspective view illustrating an electrode plate for electrochemical measurements in Embodiment 5.
Figure 21:
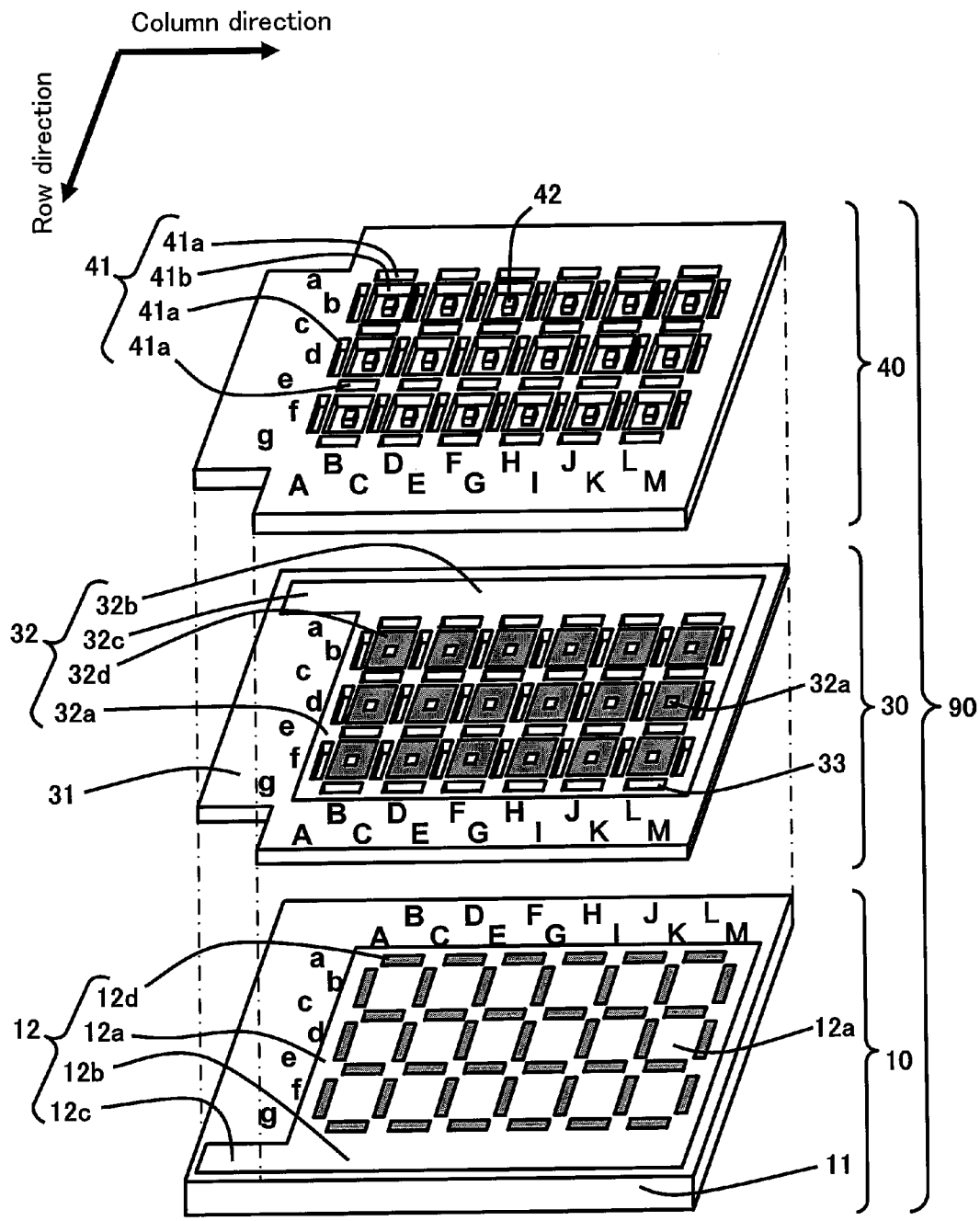
FIG. 21 shows an exploded perspective view illustrating the electrode plate for electrochemical measurements in Embodiment 5.

FIG. 20 shows a perspective view illustrating the electrode plate for electrochemical measurements 90 of the present Embodiment. In the present Embodiment, the electrode plate for electrochemical measurements is different from that of Embodiment 1 in that a covering insulator 42 is formed on the first electrode body 32 within the upper layer through-hole 41b. FIG. 21 shows an exploded perspective view illustrating the electrode plate for electrochemical measurement of the present Embodiment. The covering insulator 42 formed on the upper layer 40 covers a part of the region of the first electrode body 32 exposed from the upper layer through-holes 41b. The part covered by the covering insulator 42 is prevented from contacting with the sample solution, and serves as an electrical signal transmission part 32a to execute transmission of the kinetic current at the first electrode body 32d to the stem 32b.

Next, the relationships of the shape, the area and arrangement of the upper layer through-holes 41a and 41b, and the covering insulator 42 will be explained.

Figure 22:
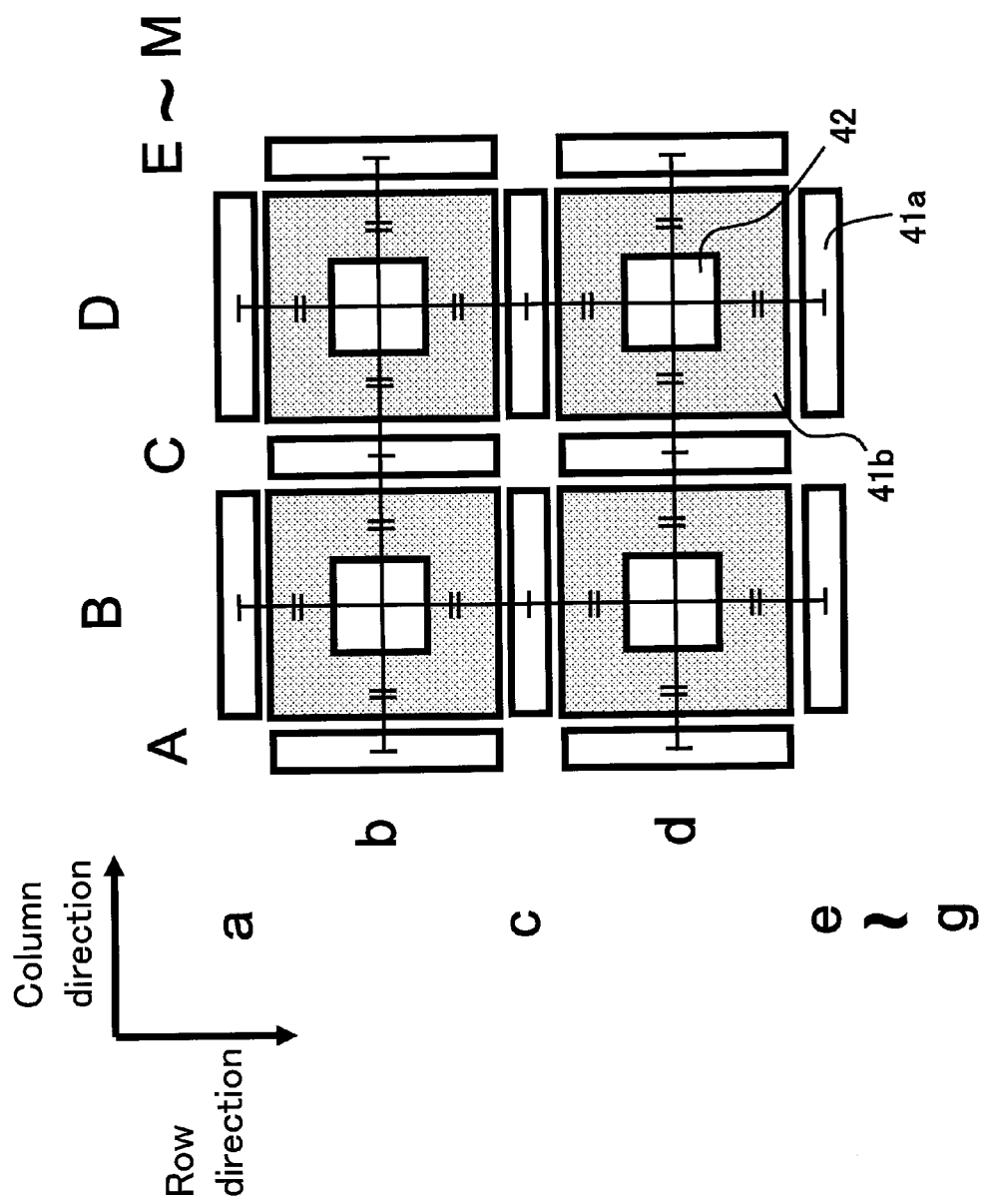
FIG. 22 shows a plane view schematically illustrating the arrangement of the upper layer through-holes and the covering insulator of the electrode plate for electrochemical measurements in Embodiment 5.

FIG. 22 shows a top view illustrating arrangement of the upper layer through-holes 41a and 41b, and covering insulator 42 in a part of the upper layer 40 of the present Embodiment. In FIG. 22, for the sake of expedience, only a part of the exposed first electrode 32d is gray-colored. The shapes of the outer edge of the upper layer through-holes 41b and the outer edge of the covering insulator 42 are on a similar relationship, and share a common center point. The part not covered by the covering insulator 42 in the upper layer through-holes 41b allows the first electrode 32d to be exposed. Furthermore, the upper layer through-holes 41a allow the second electrode body to be exposed. Also in this Embodiment, the area of the first electrode 32d exposed from the upper layer 40 is equal to total area of the second electrodes 12d therearound, similarly to Embodiment 1. In order to adjust the area of the first electrode 32d, the covering insulator 42 is formed on the first electrode 32 after adjusting the size thereof. With regard to the effects of forming the covering insulator 42, the present Embodiment is advantageous in facilitating pattern designing so as to make the area of the first electrode 32d equal to total area of the four second electrodes 12d therearound which form an electrode pair. Also in the present Embodiment, similar effects to those in Embodiment 1 are achieved.

Embodiment 6

Figure 23:
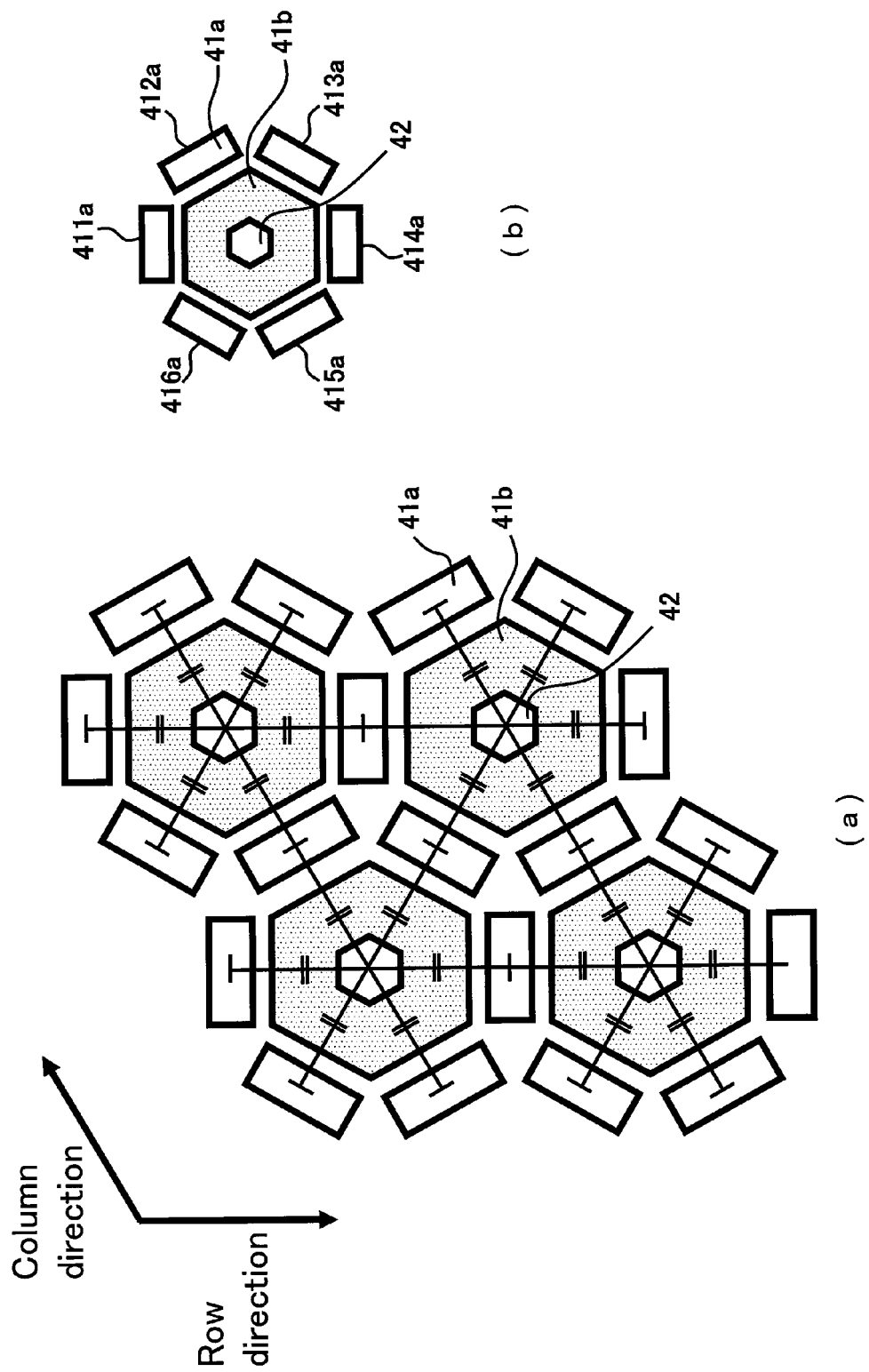
FIGS. 23(*a*) and 23(*b*) shows a plane view schematically illustrating the arrangement of the upper layer through-holes and the covering insulator of the electrode plate for electrochemical measurements in Embodiment 6.

FIG. 23 shows a top view illustrating arrangement of the upper layer through-holes 41a and 41b, and the covering insulator 42 in a part of the upper layer 40 of the present Embodiment. The electrode plate for electrochemical measurements of the present Embodiment is different from the electrode plate for electrochemical measurements of Embodiment 4 only in that the covering insulator 42 is formed on the first electrode inside the upper layer through-hole 41b. According to the present Embodiment, in the case of polygons such as regular hexagon accompanied by difficulty in adjusting the area thereof, adjusting the size of the covering insulator 42 leads to advantages in facilitating pattern designing so as to readily make the area of the first electrode equal to total area of the four second electrodes therearound, in addition to the effects as achieved by Embodiment 4.

In the embodiments described in the foregoing, the cases in which two working electrodes (in general, oxidation electrode and reduction electrode; first electrode and second electrode herein) are formed as the working electrode are demonstrated, but the present invention is not limited thereto, and constructions in which other electrode is additionally formed, and two or more working electrodes are used arbitrarily in combination are also acceptable. The redox cycle reaction is allowed to proceed between two electrodes using the electrode plate for electrochemical measurements having such a construction, while other electrode may be used to allow a reaction for eliminating interfering substances contained in the sample solution to proceed. The electrode plate for electrochemical measurements having such a construction can exclude electric current response of interfering substances, and is thus suitable for analyses of sample solutions containing several types of components. Therefore, it is suitable for analyses of biological samples constituted with a variety of components.

It should be noted that, using an electrode plate for electrochemical measurements having a similar construction to those in the Embodiments described above, there are two types of methods: a method in which the first electrode body 32 is used as an oxidation electrode body while the second electrode body 12 is used as a reduction electrode body; and a method in which the second electrode body 12 is used as an oxidation electrode body, while the first electrode body 32 is used as a reduction electrode body.

Moreover, in the foregoing Embodiments, only six cases, i.e.: the case in which the upper layer through-holes 41b have a square shape, and the number of the rectangular upper layer through-holes 41a arranged therearound is four (Embodiment 1); the case in which the upper layer through-holes 41a have a square shape, and the number of the rectangular upper layer through-holes 41b arranged therearound is four (Embodiment 2); the case in which the upper layer through-holes 41b have a square shape, and the number of the three-divided upper layer through-holes 41a arranged therearound is four (Embodiment 3); the case in which the upper layer through-holes 41b have a regular hexagonal shape, and the number of the rectangular upper layer through-holes 41a arranged therearound is six (Embodiment 4); the case in which the upper layer through-holes 41b have a square shape, the outer edge includes therein the covering insulator 42 having a similar shape, and the number of the rectangular upper layer through-holes 41a arranged therearound is four (Embodiment 5); and the case in which the upper layer through-holes 41b have a regular hexagonal shape, the outer edge includes therein the covering insulator 42 having a similar shape, and the number of the rectangular upper layer through-holes 41a arranged therearound is six (Embodiment 6) are demonstrated. However, the present invention is not limited thereto, and rectangle or other polygon would be acceptable as long as the area of each first electrode is identical to total area of the plurality of second electrodes arranged therearound, and any distance between adjacent sides is constant. However, the number of the side being excessively large is not preferred since the number of the electrodes arranged therearound also increases. Therefore, the shape is preferably square or regular hexagon. As a matter of fact, the first electrode and the second electrode may be counterchanged in the construction. In addition, when the covering insulation layer is used to adjust the electrode area, the areas of the first electrode and the second electrode can be readily adjusted.

The substrate for electrochemical measurements of the present invention enables a substance to be detected by: bringing the first electrode 32d and the second electrode 12d into contact with a sample solution containing a redox agent such as an enzyme that oxidizes or reduces the substance, and an electronic mediator; applying a voltage to the first electrode 32d and the second electrode 12d; and measuring the electric current that flows the first electrode body 32 or the second electrode body 12, and further, the substance concentration can be quantified utilizing the dependence of the electric current value to the concentration of the substance.

EXAMPLES

Hereinafter, manufacture of electrode plates for electrochemical measurements of Examples and Comparative Examples, and electrochemical determination of oxidative/reductive substance contained in a sample solution carried out according to the present invention will be described.

Example 1

Electrode Body of Example 1

Figure 15:
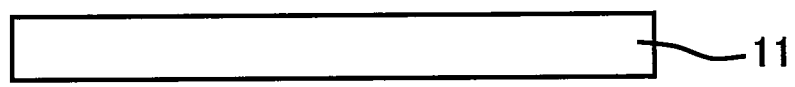
FIGS. 15(*a*)-15(*d*) show a cross-sectional view illustrating the steps of manufacturing electrode plates for electrochemical measurements according to Examples 1 and 3.
Figure 15:
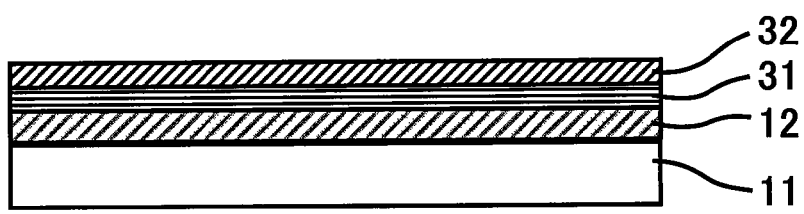
Figure 15:
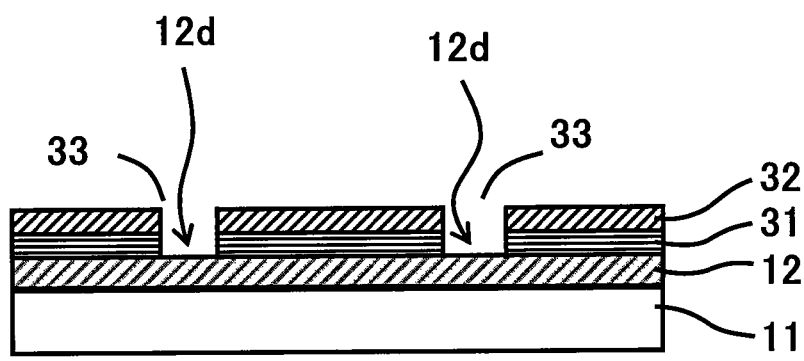
Figure 15:
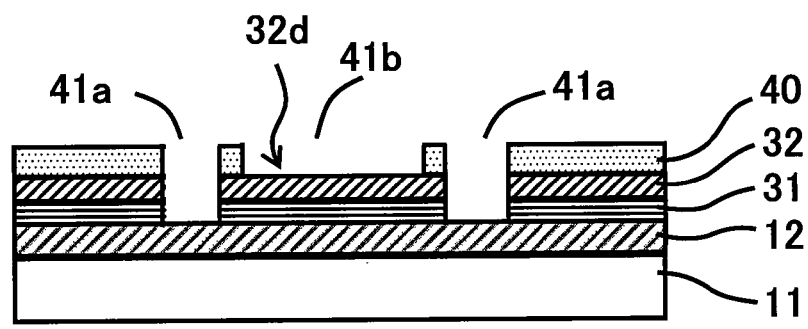

In Example 1, the electrode plate for electrochemical measurements 1 according to the first embodiment was manufactured. The number of the upper layer through-holes 41 is different from that of the electrode plate for electrochemical measurements 1 shown in FIG. 1. FIG. 15 shows a cross-sectional view illustrating the manufacturing step of the electrode plate. First, a silicon substrate (manufactured by Shin-Etsu Chemical Co.,) having a thickness of 0.5 mm with a $SiO_2$ film having a thickness of 1 μm formed on the surface thereof was used as a substrate for the lower layer (FIG. 15(a)), and attached to a prescribed position in a sputtering apparatus (manufactured by ULVAC, Inc.) together with a metal mask having a pattern of the second electrode body 12. Then, film formation was serially carried out with chromium, and gold.

In an argon atmosphere at a pressure of 1.3 Pa, sputtering was effected with chromium for 10 sec, and with gold for 50 sec, and then a total film thickness of 130 nm was yielded to obtain the second electrode body 12. Next, using a plasma CVD apparatus (manufactured by ULVAC, Inc.) on the upper face of the second electrode body 12, $SiO_2$ was deposited. As a result of the deposition carried out under a film forming condition of a silane gas flow rate being 10 sccm, an $N_2O$ gas flow rate being 200 sccm, at a pressure of 80 Pa, a power of 50 W, and a substrate temperature of 300° C. for 5 min, a 430 nm $SiO_2$ film was formed, and then substrate 31 that is an insulating layer was obtained. Similar steps to those in pattern formation of the second electrode body 12 were conducted thereon to obtain the first electrode body 32 (FIG. 15(b)).

Next, for the purpose of improving adhesiveness between the substrate 31 and the resist material, a pre-treatment material (manufactured by Microchem Corp.: MCC PRIMER 80/20) was applied by a spin coating method, followed by baking at 110° C. for 180 sec. A resist material (manufactured by Tokyo Ohka Kogyo Co., Ltd.: TSMR-8900LB) was applied thereon to give a thickness of 2 to 3 μm. This substrate following resist application and film formation was placed in an oven, and a prebaking step was carried out at 100° C. for 30 min, followed by a post baking step under a condition of 120° C. for 30 min.

Thereafter, close contact and exposure were carried out with a mask aligner (manufactured by MIKASA Co., LTD) using a chromium mask having a pattern of the substrate through-holes 33 for 60 sec. Subsequently, development was carried out in a developing solution at 25° C. for 120 sec, followed by water washing, and drying to transfer the mask pattern to the resist. Next, the substrate was subjected to etching with gold, and then chromium using an argon milling apparatus (Hitachi High-Technologies Corporation: E-3500), at an argon gas flow rate of 125 sccm, a pressure of 0.03 Pa, and at a beam electric current of 90 mA. Subsequently, etching with $SiO_2$ was carried out in a reactive ion etching apparatus under a condition of a flow rate of a $C_2F_6$ gas of 25 sccm, a pressure of 0.25 Pa, and at 150 W for 15 min to form a pattern of the substrate through-holes 33 on the substrate 31 (FIG. 15(c)).

Next, after the resist was removed, a photosensitive resin material (manufactured by Kayaku Microchem Co., Ltd.: SU-8 2000) was applied by a spin coating method so as to have a thickness of 1 μm on the surface of the first electrode body 32 having the substrate through-holes 33 formed therewith, followed by baking at 70° C. for 30 min. Thereafter, using a chromium mask having an arrangement pattern of the upper layer through-holes 41a and 41b, exposure with close contact was carried out for 60 sec to transfer the mask pattern to the resin material.

After completing the transfer, development in a developing solution was carried out at 20° C. for 300 sec, followed by water washing, and drying. Thus, a pattern of the upper layer through-holes 41b (40×40 μm, 2,000 holes) to allow the first electrode 32d to be exposed, and a pattern of the upper layer through-holes 41a (40×10 μm, 4,090 holes) to allow the second electrode 12d to be exposed were formed on the upper layer 40 that is an insulating layer (FIG. 15(d)). The closest upper layer through-holes 41a and 41b were provided to give the interval (interval between the closest sides) of 5 μm. Finally, residual resin material on the electrode plate for electrochemical measurements was removed using a UV asher.

As a result, the electrode plate for electrochemical measurements 1 of this Example having a plurality of first electrodes 32d and a plurality of second electrodes 12d was obtained. Total area of the first electrodes 32d on the electrode plate for electrochemical measurements was 3.2 mm².

Comparative Example 1

Electrode Body of Comparative Example 1

Figure 16:
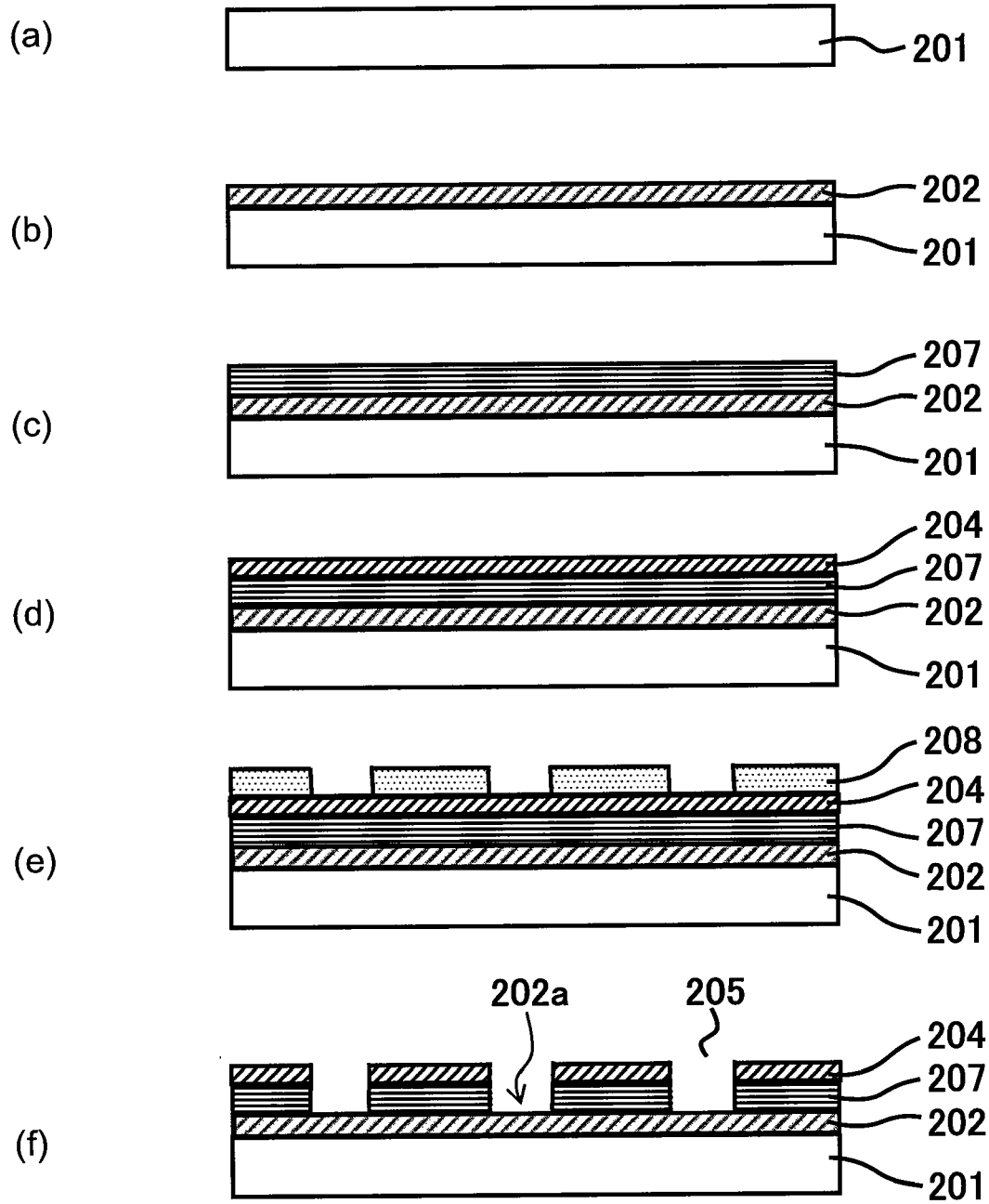
FIGS. 16(*a*)-16(*f*) show a cross-sectional view illustrating the steps of manufacturing an electrode plate for electrochemical measurements according to Comparative Example 1.
Figure 18:
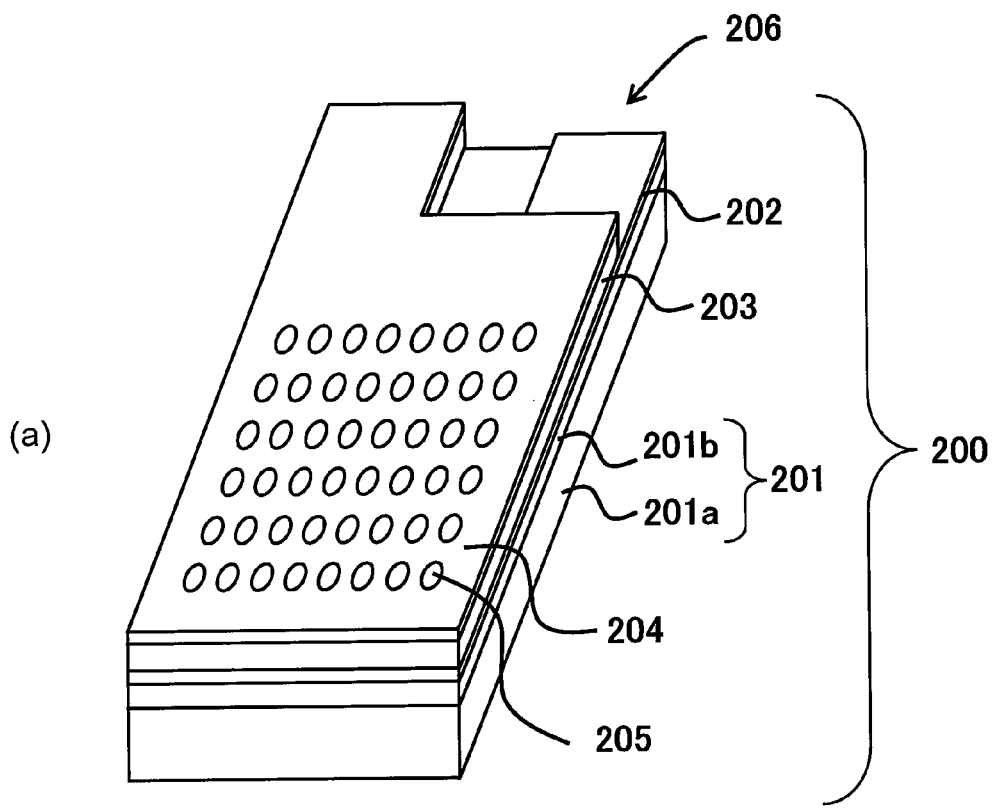
FIGS. 18(*a*) and 18(*b*) show a perspective view illustrating the construction of a conventional electrode plate for electrochemical measurements.
Figure 18:
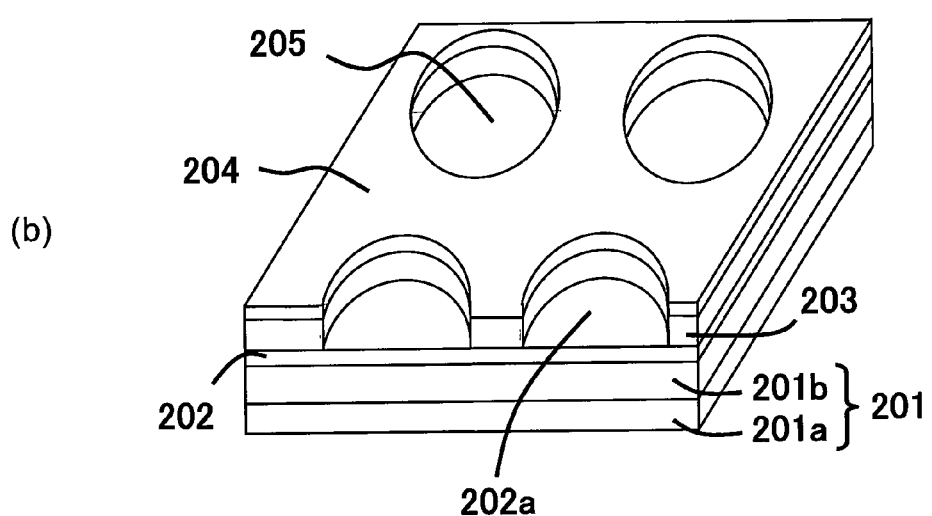

In Comparative Example 1, an electrode plate for electrochemical measurements having a conventional structure shown in FIG. 18 was manufactured. FIG. 16 shows a cross-sectional view illustrating the manufacturing step of the electrode plate for electrochemical measurements of Comparative Example 1. A silicon substrate (manufactured by Shin-Etsu Chemical Co.,) having a thickness of 0.5 mm with a SiO₂ film having a thickness of 1 μm formed on the surface thereof was used as substrate 201 shown in FIG. 16(a), which was attached to a prescribed position in a sputtering apparatus used in Example 1, and then the metal mask was set thereto. Thereafter, film formation was serially carried out with chromium, and gold. The bottom electrode body 202 was then obtained by sputtering in an argon atmosphere at a pressure of 1.3 Pa with chromium for 10 sec, and with gold for 50 sec to give a total film thickness of 130 nm (FIG. 16 (b)).

Next, a resist material used in Example 1 was applied on the substrate to give a thickness of 2 to 3 μm. This substrate following application and film formation of the resist was placed in an oven, and a prebaking step was carried out at 100° C. for 30 min. Thereafter, close contact and exposure were carried out using a chromium mask with a mask aligner used in Example 1 for 60 sec. Subsequently, development was carried out in a developing solution at 25° C. for 120 sec, followed by water washing, and drying to transfer the mask pattern to the resist 208 (FIG. 16(e)). The post baking step was carried out under a condition of 120° C. for 30 min.

Next, a resist material used in Example 1 was applied on the substrate to give a thickness of 2 to 3 μm. This substrate following application and film formation of the resist was placed in an oven, and a prebaking step was carried out at 100° C. for 30 min. Thereafter, close contact and exposure were carried out using a chromium mask with a mask aligner used in Example 1 for 60 sec. Subsequently, development was carried out in a developing solution at 25° C. for 120 sec, followed by water washing, and drying to transfer the mask pattern to the resist 208 (FIG. 15 (e)). The post baking step was carried out under a condition of 120° C. for 30 min.

The substrate having the resist 208 on which the mask pattern produced previously was transferred, was placed in an argon milling apparatus used in Example 1, and etching was serially carried out under conditions with an argon gas flow rate of 12 sccm, at a pressure of 0.03 Pa, and a beam electric current of 90 mA with gold, and with chromium. Thus etched substrate was placed in a reactive ion etching apparatus, and etching was carried out again with SiO₂ under conditions with a C₂F₆ gas flow rate of 25 sccm, at a pressure of 0.25 Pa, and at 150 W for 15 min. As a result, an electrode plate having a large number of micropores 205 exposed at the bottom face in a part of the bottom electrode body 202 (hereinafter, oxidation electrode 202a) was obtained.

Thus formed micropores 205 had a diameter of 20 μm and a distance between centers of 110 μm, in the number of formed pores of 10,000, and the surface electrode 204 formed had an area of 169 mm². Of these, total area of the bottom electrodes 202a was 3.1 mm², and thus the difference of 165.9 mm² derived from subtracting it from the surface electrode 204 formed area falls under the site in which the electrode reaction occurs on the surface electrode 204. Accordingly, the area of the surface electrode 204 became 53 times larger than the area of the bottom electrode 202a. According the steps as described above, the electrode plate for electrochemical measurements of Comparative Example 1 was obtained.

Electrochemical Measurement Using Electrode Plate for Electrochemical Measurements of Example 1 and Comparative Example 1

Apparatuses for electrochemical measurements were constructed using the electrode plate for electrochemical measurements produced in Example 1 and the electrode plate for electrochemical measurements produced in Comparative Example 1, and the response electric current of an electronic mediator was measured.

In the apparatus for electrochemical measurements, the first electrode 32d and the second electrode 12d (oxidation electrode 202a and surface electrode 204 in Comparative Example 1) were constructed so as to be exposed to the sample solution. In this Example, the first electrode 32d was used as an oxidation electrode, while the second electrode 12d was used as a reduction electrode.

In a sample solution employed, 1 mmol/l potassium ferrocyanide and 1 mmol/l potassium ferricyanide 1 mmol/l (2 mmol/l in total) as the electronic mediator were dissolved in an aqueous 50 mmol/l supporting electrolyte (potassium chloride) solution. The reference electrode employed was a silver/silver chloride electrode (manufactured by BAS Inc.,). A platinum wire was used as the auxiliary electrode.

The electrode plate for electrochemical measurements of Example 1 was connected to Bipotentiostat (manufactured by CH instruments, Inc.: ALS740A) via a lead wire, and then the reaction electric current that flows the first electrode 32d was measured by cyclic voltammetry with setting of: the potential of the first electrode 32d with respect to the reference electrode being 0 to +0.7 V; the potential of the second electrode 12d being 0 V; and the sweeping rate of the potential being 100 mV/s.

In addition, the electrode plate for electrochemical measurements of Comparative Example 1 was similarly connected to Bipotentiostat via a lead wire, and sweeping was carried out onto the silver/silver chloride electrode with the potential of the oxidation electrode 202a as a reference electrode, from 0 to +0.7 V at a sweeping rate of 100 mV/s. In this procedure, the potential of the surface electrode 204 was set to 0 V with respect to the reference electrode. As a result, in the electrode plate for electrochemical measurements of Comparative Example 1, the stationary electric current accompanying with the oxidative reaction of potassium ferrocyanide was observed at the potential of the oxidation electrode 202a being from +0.6 to +0.7 V, with the value of 22.5 μA at +0.7 V as shown in Table 1. The oxidative reaction formula of potassium ferrocyanide is as represented by the following formula 1.

$$[Fe(CN)_6]^{-4} \rightarrow [Fe(CN)_6]^{-3} + e^-$$  (formula 1)

Meanwhile, also in the electrode plate for electrochemical measurements of Example 1, the stationary electric current associated with the oxidative reaction of potassium ferrocyanide was observed at the potential of the first electrode 32d being from +0.6 to +0.7 V, with the value of 32.3 μA at +0.7 V as shown in Table 1.

TABLE 1

| | Steady state current value (μA) |
|---|---|
| Example 1 | 32.3 |
| Comparative Example 1 | 22.5 |

Figure 19:
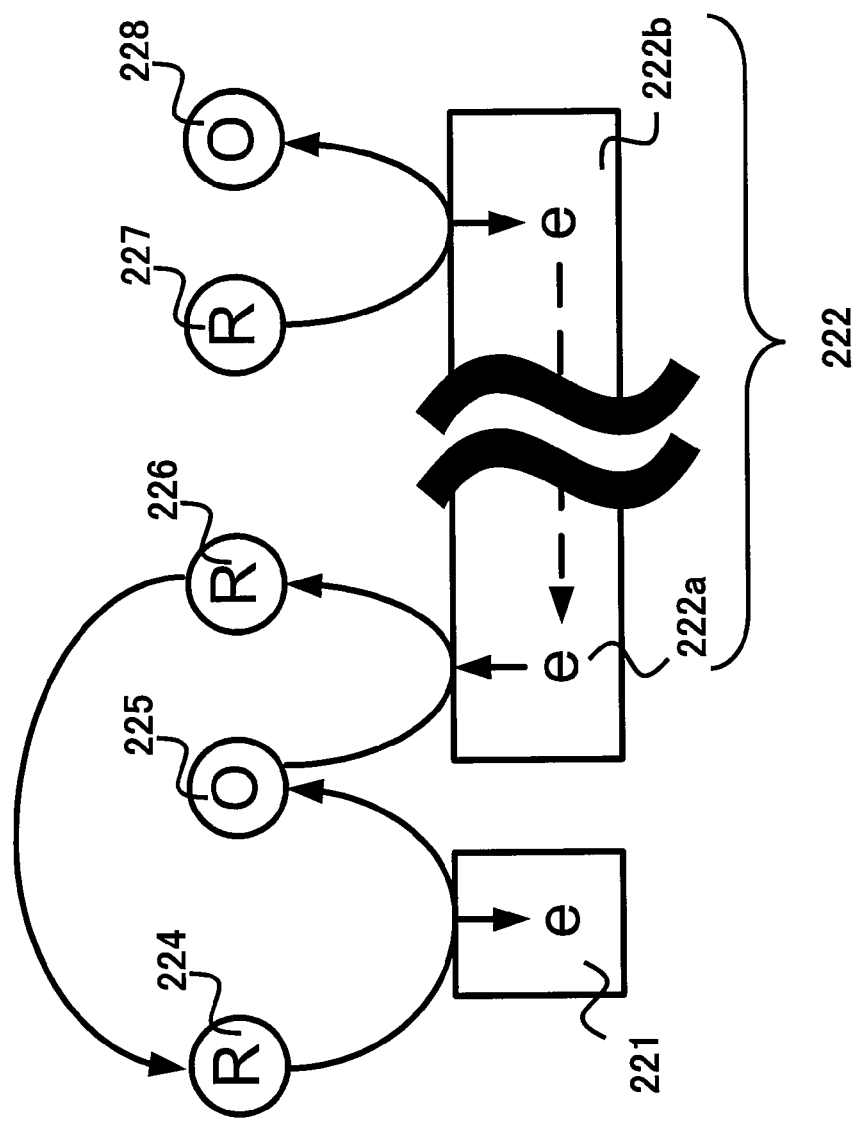
FIG. 19 shows a view schematically illustrating an oxidation-reductive reaction caused on an electrode of a conventional electrode plate for electrochemical measurements.

The greater electric current value was observed in Example as compared to the value with the electrode plate for electrochemical measurements of Comparative Example 1 because, taking into consideration the explanatory view of the self-induced redox cycle shown in FIG. 19, the electric current value of the oxidative reaction is believed to be increased since potassium ferrocyanide oxidized on the surface electrode 204 (macroelectrode 222) in Comparative Example 1 was efficiently oxidized on the first electrode 32$d$ (micro electrode 221) in Example 1. Thus, in the electrode plate for electrochemical measurements of this Example, a large number of micro electrode pairs having the same area are arranged on the substrate, therefore, uniform reaction area between respective two electrode pairs can be provided, and thus an efficient redox cycle reaction is believed to proceed between the two poles.

In addition, with respect to the oxidation electrode 202$a$ of Comparative Example 1, and the first electrode 32$d$ of Example 1, time dependency of the oxidation electric current yielded by rapidly sweeping the potential up to natural potential of +0.4 V was evaluated. During this evaluation, the potential of the surface electrode 204 of Comparative Example 1 and the second electrode 12$d$ of Example 1 was kept at 0 V. As a result, a time period of 26 sec was required until the electric current of the oxidation electrode 202$a$ of Comparative Example 1 reached the stationary state as shown in Table 2, while the first electrode 32$d$ of Example 1 reached the stationary state in 6 sec as shown in Table 2. Such observations are believed to result from the difference in the performances of the electrodes, i.e., the oxidation electrode 202$a$ of Comparative Example 1 needed a long period of time for achieving the stationary state of the surface electrode 204, but in contrast, the first electrode 32$d$ of Example 1 promptly reached the stationary state between the closest four second electrodes 12$d$.

TABLE 2

| | Time period needed until reaching to the steady state (s) |
|---|---|
| Example 1 | 6 |
| Comparative Example 1 | 26 |

From the results described above, it was proven that the electrode plate for electrochemical measurements of Example 1 enables the detection of a target substance in a sample solution with rapidity and favorable sensitivity. In addition, by producing a calibration curve beforehand, the concentration of a target substance in a sample solution can be quantified.

Example 2

Electrode Plate for Electrochemical Measurements of Example 2

Figure 17:
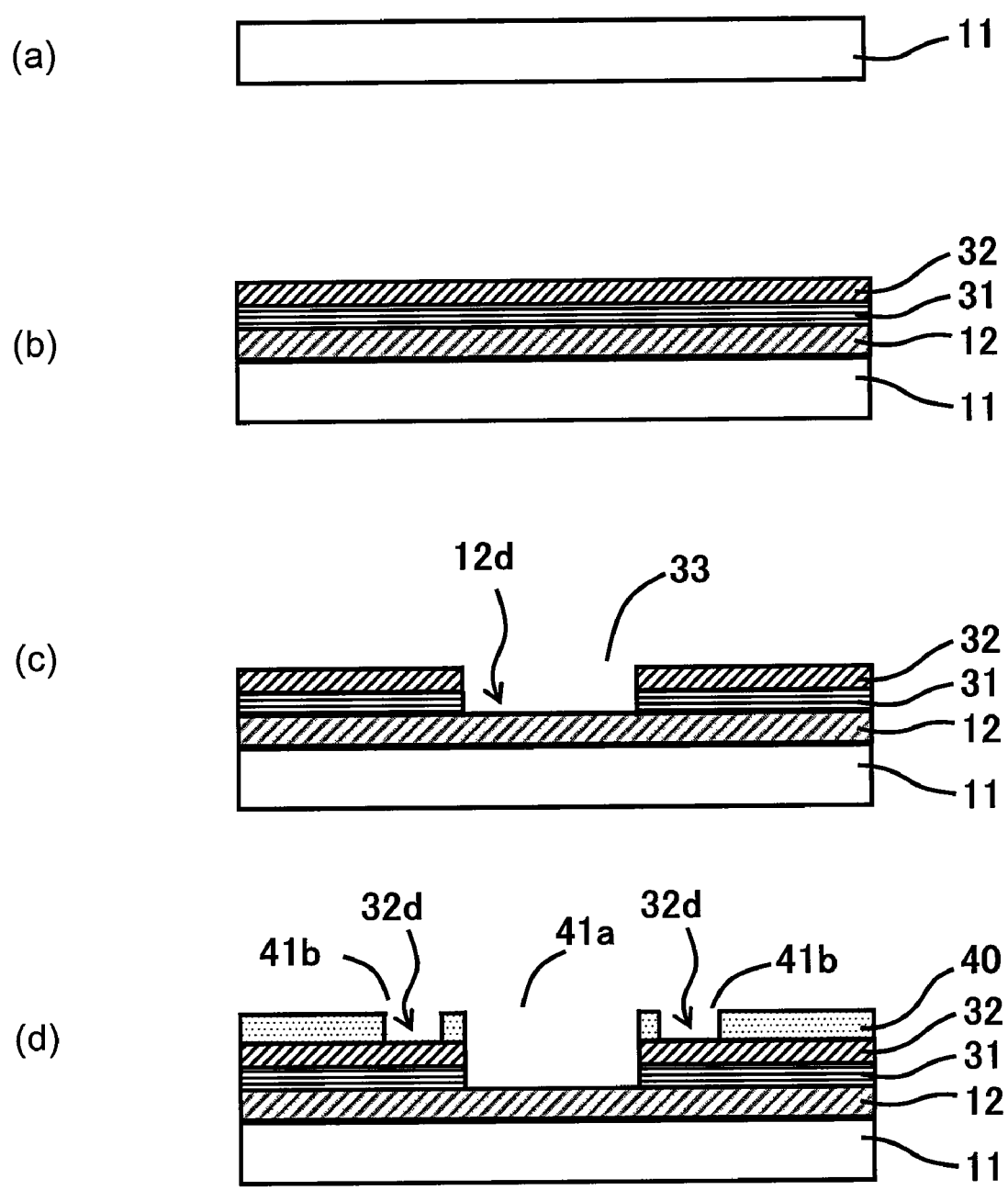
FIGS. 17(*a*)-17(*d*) show a cross-sectional view illustrating the steps of manufacturing an electrode plate for electrochemical measurements according to Example 2.

In Example 2, the electrode plate for electrochemical measurements 70 demonstrated in Embodiment 2 was manufactured. FIG. 17 shows a cross-sectional view illustrating the steps of manufacturing the electrode plate for electrochemical measurements of Example 2. The difference in the manufacturing steps of the electrode plate for electrochemical measurements of Example 1 shown in FIG. 15 only lies in that the pattern of the mask used is different due to the difference in the shape of the substrate through-holes 33 in the step shown in FIG. 17 ($c$).

An arrangement pattern of substrate through-holes 33 (40× 40 μm, 2,000 holes) was formed in the step shown in FIG. 17($c$), and an arrangement pattern of the upper layer through-holes 41$a$ (40×40 μm, 2,000 holes) and an arrangement pattern of 41$b$ (40×10 μm, 4,090 holes) were formed on the upper layer 40 in the step shown in FIG. 17($d$). A pattern of the upper layer through-holes 41$a$ (40×40 μm, 2,000 holes) to allow the second electrode 12$d$ to be exposed, and a pattern of the upper layer through-holes 41$b$ to allow the first electrode 32$d$ to be exposed were formed on the upper layer 40 that is an insulating layer. The interval between the upper layer through-holes 41$a$ and 41$b$ was 5 μm. In this Example, total area of the second electrodes 12$d$ was 3.2 mm$^2$. According to the steps described above, the electrode plate for electrochemical measurements of Example 2 was obtained.

Example 3

Electrode Plate for Electrochemical Measurements of Example 3

In Example 3, the electrode plate for electrochemical measurements 80 demonstrated in Embodiment 3 was manufactured. The manufacturing steps were almost similar to those in Example 1 shown in FIG. 15. This Example differs from Example 1 in that the arrangement pattern of the mask used in manufacture is different. The mask used in the step shown in FIG. 15($c$) has an arrangement pattern of the substrate through-holes 33 (8×8 μm, 2,130 holes), while the mask used in the step shown in FIG. 15($d$) has arrangement patterns of the upper layer through-holes 41$a$ (8×8 μm, 2,130 holes) and 41$b$ (96×96 μm, 300 holes). In these mask patterns, three-divided upper layer through-holes 41$a$ were arranged along one side of one upper layer through-holes 41$b$, and each three-divided four upper layer through-holes 41$a$ were arranged around one upper layer through-holes 41$b$, as shown in FIG. 8. In addition, the interval between the upper layer through-holes 41$a$ and 41$b$ was 10 μm, while the interval between the closest upper layer through-holes 41$b$ was 5 μm. In this Example, total area of the first electrodes 32$d$ was 2.8 mm$^2$. According to the steps described above, the electrode plate for electrochemical measurements of Example 3 was obtained.

Comparative Example 2

Electrode Plate for Electrochemical Measurements of Comparative Example 2

In Comparative Example 2, an electrode plate with each first electrode 32$d$ having an area of much larger than 10,000 μm$^2$ was manufactured. The area of each first electrode 32$d$ in this Comparative Example was 57,600 μm$^2$. FIG. 15 shows a cross-sectional view illustrating manufacturing steps of the electrode plate for electrochemical measurements of Example 3. The manufacturing steps of this Example were similar to those in Example 3, but differ in that the mask having an arrangement pattern of the substrate through-holes 33 (20×20 μm, 2,130 holes) used in the step shown in FIG. 15($c$), and a mask having an arrangement pattern of the upper layer through-holes 41a (20×20 μm, 2,130 holes) and 41b (240×240 μm, 50 holes) in the step shown in FIG. 15 (d) were used. In these mask patterns, three-divided upper layer through-holes 41a were arranged along one side of one upper layer through-holes 41b, and each three-divided four upper layer through-holes 41a were arranged around one upper layer through-holes 41b, as shown in FIG. 8. In addition, the interval between the upper layer through-holes 41a and 41b was 10 μm, while the interval between the closest upper layer through-holes 41b was 5 μm. In this Comparative Example, the area of the formed first electrodes 32d was 2.9 mm². According to the steps described above, the electrode plate for electrochemical measurements of Comparative Example 2 was obtained.

Example 4

Electrode Plate for Electrochemical Measurements of Example 4

In Example 4, an electrode plate for electrochemical measurements of Embodiment 6 was manufactured. This electrode plate is characterized by including the upper layer through-holes 41b having a regular hexagonal shape on the plane view, and including inside thereof a covering insulator the outer edge of which has a similar shape.

Figure 24:
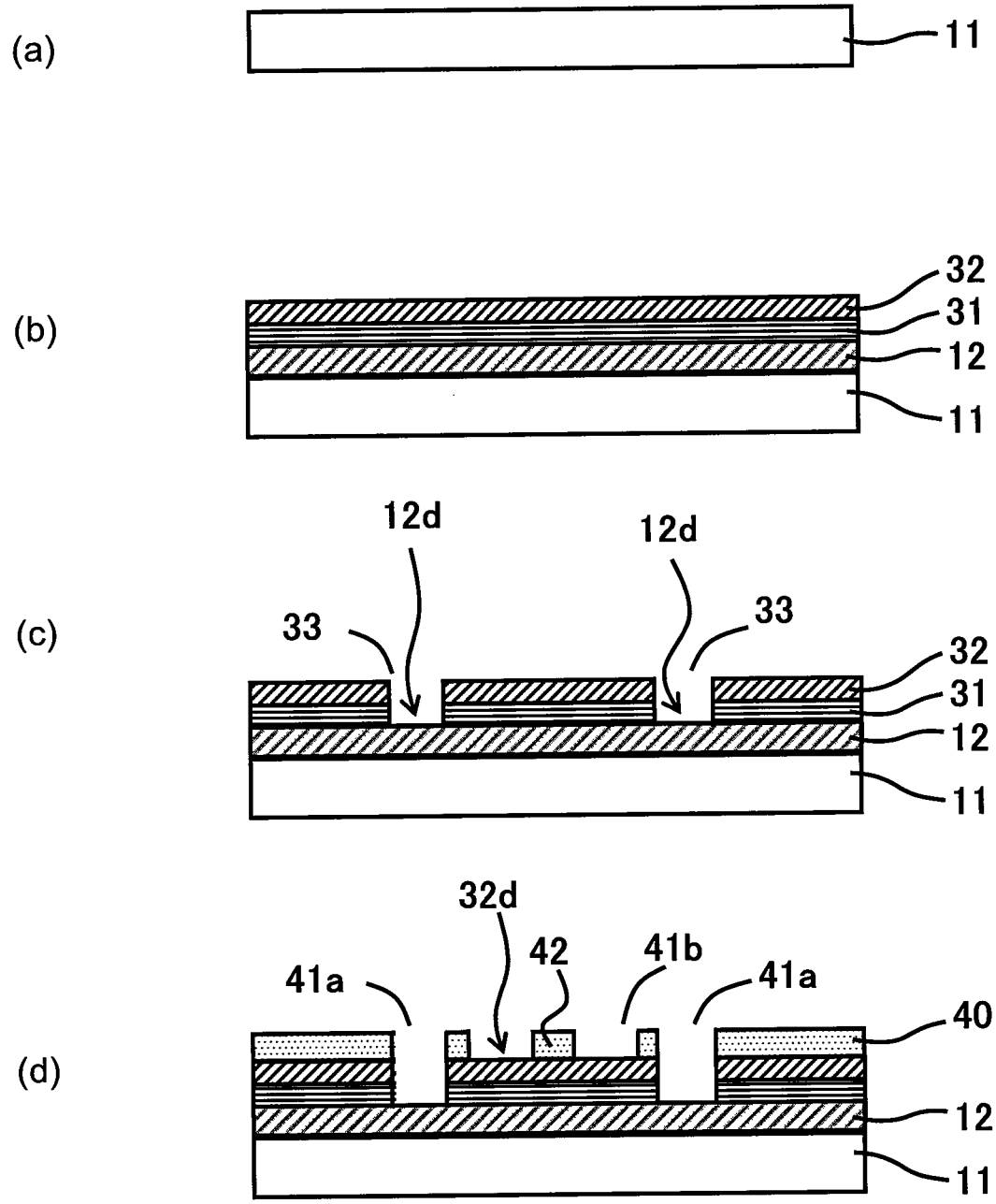
FIGS. 24(*a*)-24(*d*) show a cross-sectional view illustrating the steps of manufacturing an electrode plate for electrochemical measurements according to Example 4.

FIG. 24 shows a cross-sectional view illustrating the manufacturing steps of the electrode plate for electrochemical measurements of this Example. The manufacturing steps of this Example were different from those of Example 1 in that its pattern was transferred to a photosensitive resin material using a chromium mask having a pattern of the upper layer through-holes 41a and 41b, and the covering insulator 42 in the step of forming the upper layer shown in FIG. 24(d). Additionally, with respect to the manufacturing method, the difference lies only in that a plasma CVD process was employed for forming the substrate 31 in Example 1, but a sputtering process was employed in place thereof in this Example. Only the difference from the manufacturing steps of Example 1 will be explained below.

A substrate on which the second electrode body 12 was formed was attached to a prescribed position in a sputtering apparatus (manufactured by ULVAC, Inc.), and deposition was permitted for 25 min at an oxygen gas flow rate of 5 sccm, an argon gas flow rate of 5 sccm, a pressure of 0.3 Pa, a power of 500 W, an anode electric current of 0.35 A and an anode voltage of 2.21 kV, with the distance between the target and the substrate being 50 mm to form the substrate 31. The following steps were similar to those in Example 1, and then a photosensitive resin material was applied on the substrate surface on which the first electrode body 32 was formed.

Next, the pattern of the upper layer through-holes 41 and the covering insulator 42 as shown in FIG. 23 were transferred to the photosensitive resin material, and thus the electrode plate for electrochemical measurements of this Example was obtained via a step of forming the upper layer through-holes 41 and the covering insulator 42.

The pattern formed on the upper layer 40 included the upper layer through-holes 41b (regular hexagon with one side of 40 μm, 1,200 holes) and the upper layer through-holes 41a (40×10 μm, 3,041 holes), with the pattern of the covering insulator 42 (regular hexagon with one side of 30 μm, 1,200 holes). The upper layer through-holes 41b were formed so as to get the closest to six upper layer through-holes 41a, and the interval from the closest side was 5 μm. In this Example, total area of the first electrodes 32d was 2.9 mm².

According to the steps described above, the electrode plate for electrochemical measurements of Example 4 was obtained.

Electrochemical Measurement Using Electrode Plate for Electrochemical measurements of Examples 2 to 4

Next, apparatuses for electrochemical measurements were constructed using the electrode plates for electrochemical measurements of Examples 2 to 4 and Comparative Example 2 under similar conditions to the measurement in Example 1, and the oxidation electric current of potassium ferrocyanide was determined. As a result, under the same condition as that of the measuring method in Example 1, the steady state electric current values shown in Table 3 were observed in the apparatuses for electrochemical measurements.

TABLE 3

| | Steady state current value (μA) |
|---|---|
| Example 2 | 30.2 |
| Example 3 | 29.3 |
| Comparative Example 2 | 23.1 |
| Example 4 | 27.0 |

The steady state electric current values for the oxidation reaction of potassium ferrocyanide observed in the apparatuses for electrochemical measurements of Examples 2 to 4 were greater than that observed in connection with Comparative Example 2.

Moreover, as shown in Table 4, the time needed until the reaction reached its steady state on the first electrodes 32d of Examples 2 to 4 was shorter than the time for Comparative Example 2. From this observation, it was surmised that unexpected reaction proceeded at a position away from the second electrode 12d due to the large area of the first electrode 32d.

TABLE 4

| | Time needed until reaching to the steady state (s) |
|---|---|
| Example 2 | 8 |
| Example 3 | 9 |
| Comparative Example 2 | 18 |
| Example 4 | 12 |

From the foregoing results, it was proven that a target substance in a sample solution can be detected with rapidity and favorable sensitivity also with the electrode plates for electrochemical measurements of Examples 2 to 4, in a similar manner to the electrode plate for electrochemical measurements of Example 1. In addition, by producing a calibration curve beforehand, quantifying a target substance in a sample solution is also enabled.

From the description hereinabove, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the construction and/or function of the present invention can be substantially altered without departing from the spirit thereof.

The method of detecting or quantifying a target substance contained in a sample solution according to the present invention can be utilized in methods of quantifying a substance contained in a biological sample such as sucrose, glucose. In addition, the method can be utilized in methods of quantifying the concentration of a toxic substance contained in drinking water in a trace amount.

Additionally, the electrode plate for electrochemical measurements according to the present invention can be also utilized in an apparatus for electrochemical measurements that construct an electrochemical sensor, or a detector of liquid chromatogram.

What is claimed is:

1. A method of detecting or quantifying a target substance contained in a sample solution with an apparatus for electrochemical measurements comprising a reference electrode, an auxiliary electrode and an electrode plate for electrochemical measurements, or a counter electrode and an electrode plate for electrochemical measurements, wherein:

the sample solution contains an electronic mediator,
the electrode plate for electrochemical measurements consists of a first electrode plate or a second electrode plate,
the first electrode plate comprising
a substrate made of an insulator,
an upper layer made of an insulator provided on an upper face of the substrate,
a lower layer made of an insulator provided on a lower face of the substrate,
a first electrode body sandwiched between the upper face of the substrate and the upper layer, and
a second electrode body sandwiched between the lower face of the substrate and the lower layer, wherein:
the substrate has a plurality of substrate through-holes;
the upper layer has a plurality of upper layer through-holes;
the first electrode body has a plurality of first electrodes composed of a portion exposed from an upper face of the upper layer via the upper layer through-hole;
the second electrode body has a plurality of second electrodes composed of a portion exposed from the upper face of the upper layer via the upper layer through-hole and the substrate through-hole, and wherein:
on a plane view,
any of the plurality of substrate through-holes does not overlap with the first electrodes;
four or more second electrodes having substantially the same area are disposed around the each first electrode, with an even distance between centers of the first electrode and each of the second electrodes; and
two first electrodes having substantially the same area are disposed around the each second electrode, with an even distance between centers of the second electrode and each of the first electrodes, further wherein:
the area of the each first electrode and total area of the second electrodes therearound are substantially the same,
the second electrode plate comprising
a substrate made of an insulator,
an upper layer made of an insulator provided on an upper face of the substrate,
a lower layer made of an insulator provided on a lower face of the substrate,
a first electrode body sandwiched between the upper face of the substrate and the upper layer, and
a second electrode body sandwiched between the lower face of the substrate and the lower layer, wherein:
the substrate has a plurality of substrate through-holes extending through from the upper face to the lower face of the substrate;
the upper layer has a plurality of upper layer through-holes extending through from the upper face to the lower face of the upper layer;
the first electrode body has a plurality of first electrodes composed of a portion exposed from an upper face of the upper layer via the upper layer through-hole; and
the second electrode body has a plurality of second electrodes composed of a portion exposed from the upper face of the upper layer via the upper layer through-hole and the substrate through-hole, and wherein:
on a plane view,
any of the plurality of substrate through-holes does not overlap with the first electrodes;
four or more first electrodes having substantially the same area are disposed around the each second electrode, with an even distance between centers of the second electrode and each of the first electrodes;
two second electrodes having substantially the same area are disposed around the each first electrode, with an even distance between centers of the first electrode and each of the second electrodes; and
the area of the each second electrode and total area of the first electrodes therearound are substantially the same,
said method comprising the steps of:
bringing the reference electrode, the auxiliary electrode and the electrode plate for electrochemical measurements, or the counter electrode and the electrode plate for electrochemical measurements into contact with the sample solution;
sweeping a positive potential to either one of the first electrode body and the second electrode body, and applying a negative potential to the other one, or applying a positive potential to either one of the first electrode body and the second electrode body, and sweeping a negative potential to the other one, to measure the electric current that flows between the first electrode body and the second electrode body; and
calculating the amount of the target substance or detecting the target substance on the basis of the electric current.

2. The method according to claim 1, wherein a plurality of covering insulators that adjust the area of the portion exposed from the upper face of the upper layer are provided on the first electrode body.

3. The method according to claim 2, wherein the covering insulator is provided on the each first electrode, and
on a plane view,
the each first electrode and the covering insulator provided thereon share a common center point, and the outer edges of them have similar shapes.

4. The method according to claim 1, wherein the each first electrode has a square shape on a plane view.

5. The method according to claim 1, wherein the each first electrode has a regular hexagonal shape on a plane view.

6. The method according to claim 1, wherein the first electrode body is composed of a metal plate including all the plurality of the first electrodes.

7. The method according to claim 1, wherein the second electrode body is composed of a metal plate including all the plurality of the second electrodes.

8. An apparatus for electrochemical measurements comprising a reference electrode, an auxiliary electrode and an electrode plate for electrochemical measurements, or a counter electrode and an electrode plate for electrochemical measurements, wherein:
the electrode plate for electrochemical measurements consisting of a first electrode plate or a second electrode plate, wherein the first electrode plate comprises
a substrate made of an insulator,
an upper layer made of an insulator provided on an upper face of the substrate,
a lower layer made of an insulator provided on a lower face of the substrate,
a first electrode body sandwiched between the upper face of the substrate and the upper layer, and
a second electrode body sandwiched between the lower face of the substrate and the lower layer, wherein:
the substrate has a plurality of substrate through-holes extending through from the upper face to the lower face of the substrate;
the upper layer has a plurality of upper layer through-holes extending through from the upper face to the lower face of the upper layer;
the first electrode body has a plurality of first electrodes composed of a portion exposed from an upper face of the upper layer via the upper layer through-hole; and
the second electrode body has a plurality of second electrodes composed of a portion exposed from the upper face of the upper layer via the upper layer through-hole and the substrate through-hole, and wherein:
on a plane view,
any of the plurality of substrate through-holes does not overlap with the first electrode;
four or more second electrodes having substantially the same area are disposed around the each first electrode, with an even distance between centers of the first electrode and each of the second electrodes; and
two first electrodes having substantially the same area are disposed around the each second electrode, with an even distance between centers of the second electrode and each of the first electrodes, further wherein:
the area of the each first electrode and total area of the second electrodes therearound are substantially the same,
the second electrode plate comprising
a substrate made of an insulator,
an upper layer made of an insulator provided on an upper face of the substrate,
a lower layer made of an insulator provided on a lower face of the substrate,
a first electrode body sandwiched between an upper face of the substrate and the upper layer, and
a second electrode body sandwiched between a lower face of the substrate and the lower layer, wherein:
the substrate has a plurality of substrate through-holes; and
the upper layer has a plurality of upper layer through-holes, and wherein:
on a plane view,
any of the plurality of substrate through-holes does not overlap with the first electrode;
four or more first electrodes having substantially the same area are disposed around the each second electrode, with an even distance between centers of the second electrode and each of the first electrodes;
two second electrodes having substantially the same area are disposed around the each first electrode, with an even distance between centers of the first electrode and each of the second electrodes; and
the area of the each second electrode and total area of the first electrodes therearound are substantially the same.

9. An electrode plate for electrochemical measurements comprising a substrate made of an insulator,
an upper layer made of an insulator provided on an upper face of the substrate,
a lower layer made of an insulator provided on a lower face of the substrate,
a first electrode body sandwiched between the upper face of the substrate and the upper layer, and
a second electrode body sandwiched between the lower face of the substrate and the lower layer, wherein:
the substrate has a plurality of substrate through-holes extending through from the upper face to the lower face of the substrate;
the upper layer has a plurality of upper layer through-holes extending through from the upper face to the lower face of the upper layer;
the first electrode body has a plurality of first electrodes composed of a portion exposed from an upper face of the upper layer via the upper layer through-hole;
the second electrode body has a plurality of second electrodes composed of a portion exposed from the upper face of the upper layer via the upper layer through-hole and the substrate through-hole, and wherein:
on a plane view,
any of the plurality of substrate through-holes does not overlap with the first electrode;
four or more second electrodes having substantially the same area are disposed around the each first electrode, with an even distance between centers of the first electrode and each of the second electrodes;
two first electrodes having substantially the same area are disposed around the each second electrode, with an even distance between centers of the second electrode and each of the first electrodes; and
the area of the each first electrode and total area of the second electrodes therearound are substantially the same.

10. The electrode plate for electrochemical measurements according to claim 9, wherein a plurality of covering insulators that adjust the area of the portion exposed from an upper face of the upper layer are provided on the first electrode body.

11. The electrode plate for electrochemical measurements according to claim 10, wherein
the covering insulator is provided on the each first electrode, and
on a plane view,
the each first electrode and the covering insulator provided thereon share a common center point, and the outer edge of them has a similar shape.

12. The electrode plate for electrochemical measurements according to claim 9, wherein
on a plane view,
the each first electrode has a square shape.

13. The electrode plate for electrochemical measurements according to claim 9, wherein
on a plane view,
the each first electrode has a regular hexagonal shape.

14. The electrode plate for electrochemical measurements according to claim 9, wherein the first electrode body is composed of a metal plate including all the plurality of the first electrodes.

15. The electrode plate for electrochemical measurements according to claim 9, wherein the second electrode body is composed of a metal plate including all the plurality of the second electrodes.

16. An electrode plate for electrochemical measurements comprising a substrate made of an insulator, an upper layer made of an insulator provided on an upper face of the substrate, a lower layer made of an insulator provided on a lower face of the substrate, a first electrode body sandwiched between the upper face of the substrate and the upper layer, and a second electrode body sandwiched between the lower face of the substrate and the lower layer, wherein:

the substrate has a plurality of substrate through-holes extending through from the upper face to the lower face of the substrate;

the upper layer has a plurality of upper layer through-holes extending through from the upper face to the lower face of the upper layer;

the first electrode body has a plurality of first electrodes composed of a portion exposed from an upper face of the upper layer via the upper layer through-hole;

the second electrode body has a plurality of second electrodes composed of a portion exposed from the upper face of the upper layer via the upper layer through-hole and the substrate through-hole, and wherein:

on a plane view, any of the plurality of substrate through-holes does not overlap with the first electrode;

four or more first electrodes having substantially the same area are disposed around the each second electrode, with an even distance between centers of the second electrode and each of the first electrodes;

two second electrodes having substantially the same area are disposed around the each first electrode, with an even distance between centers of the first electrode and each of the second electrodes; and the area of the each second electrode and total area of the first electrodes therearound are substantially the same.

17. The electrode plate for electrochemical measurements according to claim 16, wherein a plurality of covering insulators that adjust the area of the portion exposed from the upper face of the upper layer are provided on the second electrode body.

18. The electrode plate for electrochemical measurements according to claim 17, wherein
the covering insulator is provided on the each second electrode, and
on a plane view,
the each second electrode and the covering insulator provided thereon share a common center point, and the outer edge of them has a similar shape.

19. The electrode plate for electrochemical measurements according to claim 16, wherein
on a plane view,
the each second electrode has a square shape.

20. The electrode plate for electrochemical measurements according to claim 16, wherein
on a plane view,
the each second electrode has a regular hexagonal shape.

21. The electrode plate for electrochemical measurements according to claim 16, wherein the first electrode body is composed of a metal plate including all the plurality of the first electrodes.

22. The electrode plate for electrochemical measurements according to claim 16, wherein the second electrode body is composed of a metal plate including all the plurality of the second electrodes.

* * * * *